(12) United States Patent
Burnett et al.

(10) Patent No.: US 11,957,656 B2
(45) Date of Patent: *Apr. 16, 2024

(54) METHODS OF TREATING PRADER-WILLI SYNDROME

(71) Applicants: The Trustees of Columbia University in the City of New York, New York, NY (US); Levo Therapeutics, Inc., Skokie, IL (US)

(72) Inventors: Lisa Cole Burnett, Chicago, IL (US); Dieter Egli, New York, NY (US); Rudolph L Leibel, New York, NY (US); Sara Cotter, New York, NY (US)

(73) Assignees: The Trustees of Columbia University in the City of New York, New York, NY (US); Levo Therapeutics, Inc., Skokie, IL (US)

( * ) Notice: Subject to any disclaimer, the term of this patent is extended or adjusted under 35 U.S.C. 154(b) by 428 days.

This patent is subject to a terminal disclaimer.

(21) Appl. No.: 17/080,180

(22) Filed: Oct. 26, 2020

(65) Prior Publication Data

US 2021/0113521 A1    Apr. 22, 2021

Related U.S. Application Data

(63) Continuation of application No. 16/306,233, filed as application No. PCT/US2017/035655 on Jun. 2, 2017, now Pat. No. 10,842,775.

(60) Provisional application No. 62/375,662, filed on Aug. 16, 2016, provisional application No. 62/345,133, filed on Jun. 3, 2016.

(51) Int. Cl.

| | | |
|---|---|---|
| A61K 31/366 | (2006.01) |
| A61K 31/277 | (2006.01) |
| A61K 31/352 | (2006.01) |
| A61K 31/4015 | (2006.01) |
| A61K 31/403 | (2006.01) |
| A61K 31/4035 | (2006.01) |
| A61K 31/4162 | (2006.01) |
| A61K 31/426 | (2006.01) |
| A61K 31/437 | (2006.01) |
| A61K 31/4375 | (2006.01) |
| A61K 31/44 | (2006.01) |
| A61K 31/454 | (2006.01) |
| A61K 31/517 | (2006.01) |
| A61K 31/519 | (2006.01) |
| A61K 31/522 | (2006.01) |
| A61K 31/5513 | (2006.01) |
| A61K 31/69 | (2006.01) |
| A61K 38/08 | (2019.01) |
| A61K 38/095 | (2019.01) |
| A61K 45/06 | (2006.01) |
| A61P 43/00 | (2006.01) |
| A61K 38/00 | (2006.01) |

(52) U.S. Cl.
CPC .......... *A61K 31/366* (2013.01); *A61K 31/277* (2013.01); *A61K 31/352* (2013.01); *A61K 31/4015* (2013.01); *A61K 31/403* (2013.01); *A61K 31/4035* (2013.01); *A61K 31/4162* (2013.01); *A61K 31/426* (2013.01); *A61K 31/437* (2013.01); *A61K 31/4375* (2013.01); *A61K 31/44* (2013.01); *A61K 31/454* (2013.01); *A61K 31/517* (2013.01); *A61K 31/519* (2013.01); *A61K 31/522* (2013.01); *A61K 31/5513* (2013.01); *A61K 31/69* (2013.01); *A61K 38/08* (2013.01); *A61K 38/095* (2019.01); *A61K 45/06* (2013.01); *A61P 43/00* (2018.01); *A61K 38/00* (2013.01)

(58) Field of Classification Search
CPC .. A61K 31/366; A61K 31/277; A61K 31/352; A61K 31/4015; A61K 31/403; A61K 31/4035; A61K 31/4162; A61K 31/426; A61K 31/437; A61K 31/4375; A61K 31/44; A61K 31/454; A61K 31/517; A61K 31/519; A61K 31/522

See application file for complete search history.

(56) References Cited

U.S. PATENT DOCUMENTS

| | | | |
|---|---|---|---|
| 10,842,775 B2 * | 11/2020 | Burnett | A61K 31/277 |
| 2006/0062859 A1 | 3/2006 | Blum et al. | |
| 2008/0250516 A1 | 10/2008 | Gekakis et al. | |
| 2012/0289511 A1 | 11/2012 | Alam | |

FOREIGN PATENT DOCUMENTS

| | | |
|---|---|---|
| CN | 1918164 | 2/2007 |
| CN | 101361754 | 4/2013 |
| EP | 2322163 | 5/2011 |
| JP | 2014-513694 A | 6/2014 |

(Continued)

OTHER PUBLICATIONS

Doseyici, S. et al., "The effects of forskolin and rolipram on cAMP, cGMP and free fatty acid levels in diet induced obesity", Biotechnic & Histochemistry, 2014, vol. 89, No. 5, pp. 388-392, DOI: 10.3109/10520295.2014.883463. 6 pages.

(Continued)

*Primary Examiner* — Olga N Chernyshev
(74) *Attorney, Agent, or Firm* — Amster, Rothstein & Ebenstein LLP

(57) ABSTRACT

The present invention relates to methods for regulating prohormone convertase (PC1) and compounds and treatments which increase PC1 levels, for treating Prader-Willi Syndrome (PWS).

8 Claims, 15 Drawing Sheets

(56) References Cited

FOREIGN PATENT DOCUMENTS

| WO | WO 01/35979 | 5/2001 |
|---|---|---|
| WO | WO 01/79837 | 10/2001 |
| WO | WO 03061638 | 7/2003 |
| WO | 2008127717 | 10/2008 |
| WO | WO 2010/062681 | 6/2010 |
| WO | 2011/083718 A1 | 7/2011 |
| WO | 2012/154814 A1 | 11/2012 |
| WO | WO 2014197753 | 12/2014 |
| WO | WO 2015/112568 | 7/2015 |
| WO | WO 2016077629 | 5/2016 |

OTHER PUBLICATIONS

Examination Report for corresponding Australian application No. 2017275652, dated Apr. 1, 2022. 6 pages.
Piro et al. "Chronic Exposure to GLP-1 Increases GLP-1 Synthesis and Release in a Pancreatic Alpha Cell Line (a-TC1 ): Evidence of a Direct Effect of GLP-1 on Pancreatic Alpha Cells", PLoS One, Feb. 2014, vol. 9; p. 1-14.
Jensterle et al. "Short term monotherapy with GLP-1 receptor agonist liraglutide or PDE 4 inhibitor roflumilast is superior to metformin in weight loss in obese PCOS women: a pilot randomized study" Journal of Ovarian Research. Jun. 2, 2015 (Jun. 2, 2015) vol. 8, p. 1-8.
Gabreels et al. "Attenuation of the Polypeptide 782, Prohormone Convertase PC2, and Vasopressin in the Hypothalamus of Some Prader-Willi Patients: Indications for a Processing Defect" Journal of Clinical Endocrinology and Metabolism. Feb. 1, 1998; vol. 83, p. 591-599.
"Rhythm Presents Positive Data from Phase 1 b Study of Setmelanotide for the Treatment of Genetic Obesity" Rhythm, Nov. 6, 2015.
Chen et al. "Monogenic disorders of obesity and body fat distribution" Journal of Lipid Research. Oct. 1999, vol. 40, p. 1735-1746.
Wankhade et al. "Melanocortin 4 receptor is a transcriptional target of nescient helix-loop-helix-2" Molecular and Cellular Endocrinology. Jul. 20, 2011 (Jul. 20, 2011) vol. 341, p. 39-47.
Miller et al. "Necdin, a Prader-Willi syndrome candidate gene, regulates gonadotropin-releasing hormone neurons during development" Human Molecular Genetics. Oct. 17, 2008 (Oct. 17, 2008) vol. 18, p. 248-260.
Ramos-Molina et al. "PCSK1 Variants and Human Obesity" Progress in Molecular Biology and Translational Science. Jan. 29, 2016 (Jan. 29, 2016) vol. 140, p. 47-74.
Yang et al. "Effect of Caffeine on Erectile Function via Up-Regulating Cavernous Cyclic Guanosine Monophosphate in Diabetic Rats" Journal of Andrology, Jan. 2, 2013 (Jan. 2, 2013) vol. 29, p. 586-591.
Burnett et al. "Deficiency in prohormone convertase PC1 impairs prohormone processing in Prader-Willi syndrome" The Journal of Clinical Investigation. Jan. 2017, vol. 127, p. 293-305.
International Search Report and Written Opinion dated Sep. 6, 2017 corresponding to International Patent Application No. PCT/US17/35655, 15 pages.
Wang et al., "Differentiation of hypothalamic-like neurons from human pluripotent stem cells." Journal of Clinical Investigation,125(2): 796-808, 2015.
Prader-Willi Syndrome: Study of an Important Genetic Childhood Obesity Syndrome Underway, Naomi Berrie Diabetes Center, Columbia University Medical Center, Sep. 25, 2014, retrieved from http://nbdiabetes.org/news/prader-willi-syndrome, 2 pages.
Jessica Bohonowych, PWS iPS cells are helping researchers make breakthroughs, Foundation for Prader-Willi Syndrome, retrieved from https://www.fpwr.org/blog/pws-ips-cells-are-helping-researchers-make-breakthroughs, May 29, 2014.
"About Prader-Willi Syndrome"; Prader-Willi Syndrome Association; Retrieved Nov. 29, 2018, https://www.pwsausa.org/about-pws/, 5 pages.

McCandless, S. E.; Committee on Genetics. (2011). "Clinical report—Health supervision for children with Prader-Willi syndrome." Pediatrics, 127, 195-204.
"What are the treatments for PWS?" National Instititue of Health; Retrieved Nov. 29, 2018, https://www.nichd.nih.gov/health/topics/prader-willi/conditioninfo/treatments, 4 pages.
Cassidy, S. B., & Schwartz, S. "Prader-Willi syndrome." Gene reviews. Seattle, WA: University of Washington. 2009. 42 pages.
Carrel, A. L., Myers, S. E., Whitman, B. Y., & Allen, D. B. (2002). "Benefits of long-term GH therapy in Prader-Willi syndrome: A 4-year study." Journal of Clinical Endocrinology & Metabolism, 87, 1581-1585. 5 pages.
Jackson et al, Obesity and impaired prohormone processing associated with mutations in the human prohormone convertase 1 gene; Nat Genet. Jul. 1997;16(3):303-6.
Denham M., Dottori M. (2011) Neural Differentiation of Induced Pluripotent Stem Cells. In: Neurodegeneration. Methods in Molecular Biology (Methods and Protocols), vol. 793.
Dolmetsch et al, The human brain in a dish: The promise of iPSC-derived neurons, Cell. 2011; 145(6): 831-834.
Creemers et al, Heterozygous Mutations Causing Partial Prohormone Convertase 1 Deficiency Contribute to Human Obesity, Diabetes. 2012; 61(2): 383-390.
Prabhu et al, Defective Transport of the Obesity Mutant PC1/3 N222D Contributes to Loss of Function, Endocrinology. 2014; 155(7): 2391-2401.
Use of stem cell-derived neurons to identify the molecular basis of the PWS, Foundation for Prader-Willi Syndrome, retrieved from https://www.fpwr.org/fpwr-funded-projects/use-of-stem-cell-derived-neurons-to-identify-the-molecular-basis-of-the-pws, retrieved on Nov. 29, 2018; 5 pages.
Maurice et al, Advances in targeting cyclic nucleotide phosphodiesterases, Nat Rev Drug Discov. 2014; 13(4): 290-314.
Jay H. Chung: "Metabolic benefits of inhibiting cAMP-PDEs with resveratrol", Adipocyte, vol. 1, No. 4, Oct. 1, 2012 (Oct. 1, 2012), pp. 256-258, XP055761141.
Mojca Jensterle et al: "Short term monotherapy with GLP-1 receptor agonist liraglutide or PDE 4 inhibitor roflumilast is superior to metformin in weight loss in obese PCOS women: a pilot randomized study", Journal of Ovarian Research, vol. 8, No. 1, Jun. 2, 2015 (Jun. 2, 2015), p. 32, XP021227859.
S Dhanvantari et al: 11 Coregulation of glucagon-like peptide-1 synthesis with proglucagon and prohormone convertase gene expression in enteroendocrine GLUTag ce 11s 11, Endocrinology, vol. 142, No. I, 2001, pp. 37-42, XP055761322, us ISSN: 0013-7227, DOI: 10.1210/en.142.1.37 * abstract *.
Jensterle M. et al. Short term monotherapy with GLP-1 receptor agonist liraglutide or PDE 4 inhibitor roflumilast is superior tometformin in weight loss in obese PCOS women: a pilot randomized study// Journal of Ovarian Research.—Jun. 2, 2015.—V.8.—N.32.—p. 1-8.
Piro S. et al. Chronic Exposure to GLP-1 Increases GLP-1 Synthesis and Release in a Pancreatic Alpha Cell Line (a-TC1): Evidence of a Direct Effect of GLP-1 on Pancreatic Alpha Cells// Plos one.—Feb. 28, 2014.—V.9.—N.2.—p. 1-14.
Gabreels B. A. et al. Attenuation of the Polypeptide 7B2, Prohormone Convertase PC2, and Vaso-pressin in the Hypothalamus of Some Prader-Willi Patients: Indications for a Processing Defect// Journal of Clinical Endocrinology and Metabolism.—1998.—V. 83.—N. 2.—p. 591-599. Accepted Oct. 17, 1997.
Miller N. et al. Necdin, a Prader-Willi syndrome candidate gene, regulates gonadotropin-releasing hormone neurons during development// Human Molecular Genetics.—2009.—V. 18.—N. 2.—p. 248-260. Accepted Oct. 15, 2008.
Wankhade D. et al. Melanocortin 4 Receptor is a Transcriptional Target of Nescient He-lix-Loop-Helix-2// Mol Cell Endocrinol.—Jul. 20, 2011.—V.341.—N.1-2.—p. 1-19.
Ramos-Molina B. et al. PCSK1 Variants and Human Obesity// Prog Mol Biol Transl Sci.—Jan. 29, 2016.—V.140.—p. 47-74.
Yang R. et al. Effect of Caffeine on Erectile Function via Up-Regulating Cavernous Cyclic Guanosine Monophosphate in Diabetic Rats// Journal of Andrology.—Sep./Oct. 2008.—V. 29.—N. 5.—p. 586-591,

(56) References Cited

OTHER PUBLICATIONS

Jennifer L Miller et al: "Medication Trials for Hyperphagia and Food-Related Behaviors in Prader-Willi Syndrome", Diseases, vol. 3, No. 2, 2015, pp. 78-85.
Takeo Kubota et al: "Prader-Willi Syndrome: The Disease that Opened up Epigenomic-Based Preemptive Medicine", Diseases, vol. 4, No. 1, Mar. 11, 2016 (Mar. 11, 2016), p. 15.
Supplementary European Search Report in corresponding European Application EP 17 80 7557, dated Jan. 24, 2020.
Office Action and English translation for corresponding Korean Application No. 10-2018-7038176, dated Feb. 11, 2022. 7 pages.
Perez-Aso et al. "Apremilast, a novel phosphodiesterase 4(PDE4) inhibitor, regulates inflammation through multiple cAMP downstream effectors", Arthritis Research & Therapy (2015) 17:249. 13 pages.
Michel Gallant et al. "Discovery of MK-0952, a selective PDE4 inhibitor for the treatment of long-term memory loss and mild cognitive impairment", Bioorg Med Chem Lett. Nov. 15, 2010;20(22):6387-93. 7 pages.
Miller et al., "Necdin, a Prader-Willi syndrome candidate gene, regulates gonadotropin-releasing hormone neurons during development", Human Molecular Genetics, 2009, vol. 18, No. 2, pp. 248-260. Published on Oct. 17, 2008.
Conkright, M. D. et al. Genome-Wide Analysis of CREB Target Short Article Genes Reveals A Core Promoter Requirement for cAMP Responsiveness. Molecular Cell 11, 1101-1108 (2003).
Udupi, V., Townsend, C. M. & Greeley, G. H. Stimulation of Prohormone Convertase-1 mRNA Expression by Second Messenger Signaling Systems. Biochemical and Biophysical Research Communications 246, 463-465 (1998).
Onda, T. et al. Type-specific regulation of adenylyl cyclase. Selective pharmacological stimulation and inhibition of adenylyl cyclase isoforms. J Biol Chem 276, 47785-47793, doi:10.1074/jbc.M107233200 (2001).
Liang, X. H., Vickers, T. A., Guo, S. & Crooke, S. T. Efficient and specific knockdown of small non-coding RNAs in mammalian cells and in mice. Nucleic Acids Res 39, e13, doi:10.1093/nar/gkq1121 (2011).
Sunahara, R. K. & Taussig, R. Isoforms of Mammalian Adenylyl Cyclase: Multiplicities of Signaling. Molecular Interventions 2, 168-184 (2002).
S. L. Wardlaw, Hypothalamic proopiomelanocortin processing and the regulation of energy balance. European journal of pharmacology 660, 213-219 (2011).
Fimia GM, Sassone-Corsi p. 2001. Cyclic AMP signaling. J Cell Sci 114: 1971-1972.
P. Stijnen, B. Ramos-Molina, S. O'Rahily, J. W. M. Creemers, PCSK1 mutations and human endocrinopathies: from obesity to gastrointestinal disorders. Endocrine Reviews 17, (2016).

M. Gallant et al., Discovery of MK-0952, a selective PDE4 inhibitor for the treatment of long-term memory loss and mild cognitive impairment. Bioorganic & Medicinal Chemistry Letters 20, 6387-6393 (2010).
Q. Zhang, G. J. Bouma, K. Mcclellan, S. Tobet, Hypothalamic expression of snoRNA Snord116 is consistent with a link to the hyperphagia and obesity symptoms of Prader-Willi syndrome. Int J Dev Neurosci 30, 479-485 (2012).
Y. Qi et al., Snord116 is critical in the regulation of food intake and body weight. Sci Rep 6, 18614 (2016).
V. Grinevich, M. G. Desarmenien, B. Chini, M. Tauber, F. Muscatelli, Ontogenesis of oxytocin pathways in the mammalian brain: late maturation and psychosocial disorders. Front Neuroanat 8, 164 (2014).
M. Tauber et al., The Use of Oxytocin to Improve Feeding and Social Skills in Infants With Prader-Willi Syndrome. Pediatrics 139, (2017).
G. Alvarez-Bolado, F. A. Paul, S. Blaess, Sonic hedgehog lineage in the mouse hypothalamus: from progenitor domains to hypothalamic regions. Neural development 7, 4 (2012).
S. Blaess, N. Szabo, R. Haddad-Tovolli, X. Zhou, G. Alvarez-Bolado, Sonic hedgehog signaling in the development of the mouse hypothalamus. Front Neuroanat 8, 156 (2014).
E. O. Mazzoni et al., Synergistic binding of transcription factors to cell-specific enhancers programs motor neuron identity. Nat Neurosci 16, 1219-1227 (2013).
E. S. Deneris, O. Hobert, Maintenance of postmitotic neuronal cell identity. Nat Neurosci 17, 899-907 (2014).
S. Wellek, M. Blettner, On the Proper Use of the Crossover Design in Clinical Trials: Part 18 of a Series on Evaluation of Scientific Publications. Deutsches Ärzteblatt International 109, 276-281 (2012).
E. M. Dykens, M. A. Maxwell, E. Pantino, R. Kossler, E. Roof, Assessment of Hyperphagia in Prader-Willi Syndrome. Obesity 15, 1816-1826 (2007).).
S. R. Crawford et al., The International Development of The Modified Hyperphagia Questionnaire. Value in Health 18, A761.
R. J. Kuppens, S. H. Donze, A. C. S. Hokken-Koelega, Promising effects of oxytocin on social and food-related behaviour in young children with Prader-Willi syndrome: a randomized, double-blind, controlled crossover trial. Clinical Endocrinology 85, 979-987 (2016).
P. Gumus Balikcioglu et al., Macronutrient Regulation of Ghrelin and Peptide YY in Pediatric Obesity and Prader-Willi Syndrome. The Journal of Clinical Endocrinology & Metabolism 100, 3822-3831 (2015).
R. Kaddurah-Daouk, R. Weinshilboum, N. on behalf of the Pharmacometabolomics Research, Metabolomic Signatures for Drug Response Phenotypes: Pharmacometabolomics Enables Precision Medicine. Clinical Pharmacology & Therapeutics 98, 71-75 (2015).
R. D. Beger et al., Metabolomics enables precision medicine: "A White Paper, Community Perspective". Metabolomics 12, 149 (2016).

* cited by examiner

| Table 1. | LABORATORY TESTS OBTAINED DURING THE STUDY VISIT |
|---|---|
| Metabolic profile | HbA1c, Fasting lipids, hsCRP, Adiponectin, Leptin, Metabolic profiling |
| Hormonal profile | Insulin, proinsulin; ghrelin, proghrelin; ACTH, POMC; BDNF, proBDNF; oxytocin, pro-oxytocin; TSH, T4, T3; FSH/LH, Estrogen/Testosterone; AgRP, pro-AgRP, |
| MMTT profile | Glucose, insulin, proinsulin, Free Fatty Acids, ghrelin, proghrelin, |
| Safety profile | Com Metabolic Profile, Liver Func Test, drug level, Complete hemogram, electrocardiogram |

FIG.8B

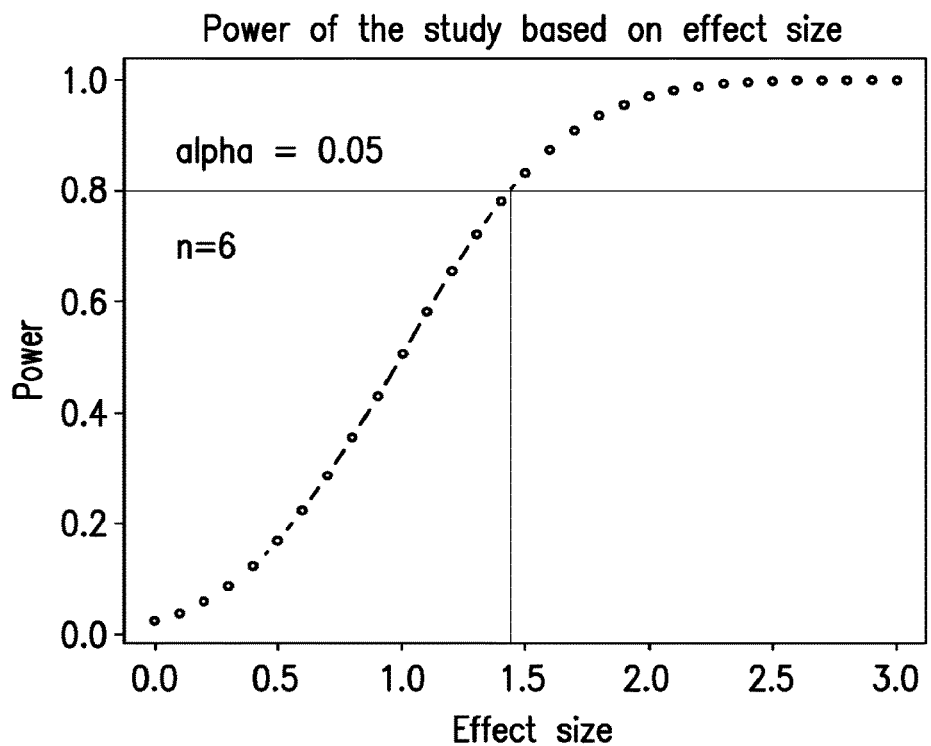

FIG.8C

METHODS OF TREATING PRADER-WILLI SYNDROME

CROSS-REFERENCE TO RELATED APPLICATIONS

The present application is a continuation of U.S. Non-Provisional patent application Ser. No. 16/306,233, filed Nov. 30, 2018, which is a 371 U.S. National Stage application of International Patent Application No. PCT/US2017/035655, filed Jun. 2, 2017, which claims priority to U.S. Provisional Patent Application No. 62/345,133 filed Jun. 3, 2016; U.S. Provisional Application No. 62/375,662 filed Aug. 16, 2016, each of which is incorporated herein by reference in its entirety.

GOVERNMENT SUPPORT

This invention was made with government support under grant DK052431 awarded by the National Institutes of Health (NIH). The government has certain rights in the present invention.

FIELD OF THE INVENTION

The present invention relates to methods for regulating prohormone convertase (PC1) and compounds and treatments which increase PC1 levels.

BACKGROUND OF THE INVENTION

Prader-Willi syndrome (PWS) is caused by a loss of paternally expressed genes in an imprinted region of chromosome 15q. Among the canonical phenotypes are hyperphagic obesity, central hypogonadism and low growth hormone. Rare microdeletion PWS patients define a 91 kb minimum critical deletion region encompassing 3 genes, including the non-coding SNORD116. We have found that NHLH2 and PC1 are downregulated in PWS iPSC-derived neurons as compared to unaffected controls. Nhlh2 and Pcsk1 transcript levels are reduced in hypothalami of fasted Snord116$^{p-/m+}$ mice.

Deficiency of Nhlh2 in mice causes obesity, hypogonadism, and growth failure. Nhlh2 promotes expression of the prohormone convertase, (PC1). Humans and mice deficient in PC1 display hyperphagic obesity, hypogonadism, decreased growth hormone, and diabetes due to impaired prohormone processing. For example, Snord116$^{p-/m+}$ mice display in vivo functional defects in prohormone processing of proinsulin, proGHRH, and proghrelin associated with reductions in PC1.

Currently there are no treatments for PWS patients and effective treatments and model systems are urgently needed.

SUMMARY OF THE INVENTION

The methods of the present invention provide for regulating prohormone convertase by administering an effective amount of a phosphodiesterase 4 inhibitor (PDE4 inhibitor or PDE4i). Expression of the prohormone convertase may be upregulated by administration of a therapeutically effective amount of a PDE4 inhibitor. The PDE4 inhibitor may be administered to a cell or to a patient with Prader-Willi syndrome. The PDE4 inhibitor may be administered to an obese subject. It is also expected that these methods will be useful for treating patients with Schaaf-Yang Syndrome and Autism Spectrum Disorder.

The PDE4 inhibitor may be administered orally, intravenously, subcutaneously, intrathecally, topically, intranasally, or to the lungs.

The PDE4 inhibitor can include, theophylline, roflumilast, apremilast, ibdulast, GSK356278, MK0952, IBMX as well as combinations of these drugs.

In certain embodiments, the PDE4 inhibitor can include any of the inhibitors from Tables 1A or Table 1B.

In additional embodiments, combinations of PDE4 inhibitors may be used in the present methods.

The methods of the present invention also include administering a therapeutically effective amount of an adenylate cyclase activator. The adenylate cyclase activator can be administered to a cell or to a patient with Prader-Willi syndrome. The adenylate cyclase activator may be administered to an obese subject.

The adenylate cyclase activator can be administered orally, intravenously, intrathecally, intranasally, topically, or to the lungs. The adenylate cyclase activator can include, Forskolin, FD1, FD2, FD3, FD4, FD5 (NKH477), FD6 as well as combinations of these drugs.

The PDE4 inhibitor may also be administered together with the adenylate cyclase activator.

The methods of the present invention also include administering a therapeutically effective amount of an MC4R agonist. The MC4R agonist can be administered to a cell or to a patient with Prader-Willi syndrome. The MC4R agonist may be administered to an obese subject.

The MC4R agonist can be administered orally, intravenously, intrathecally, intranasally, topically, or to the lungs. The MC4R agonist can include RM-493 (Setmelanotide), TTP2515, 2-aminothiazole derivatives, MK-0493, and combinations thereof. The MC4R agonist can be administered in combination with the PDE4 inhibitors and/or adenylate cyclase activators described herein.

The methods of the present invention also include methods wherein the administration results in one or more of the following improvements in the patient: decreases or ameliorates hyperphagia; increases PCSK1 levels; increases PC1 level and/or activity; decreases circulating proinsulin to insulin ratio, thus increasing insulin secretion; decreases circulating proghrelin to ghrelin ratio; decreases circulating POMC to ACTH ratio; amelioration of hypothyroidism, decreases circulating ratio of pro-oxytocin to oxytocin, thus increasing oxytocin production in the brain and increases alpha-MSH production in the brain; decreases circulating ratio of pro-BDNF to BDNF (increase brain levels of BDNF); and increases the ratio of prohormone:hormone (decreases pro-mature hormone); wherein the symptom, levels, or ratios are in reference to the patient's disease symptom, levels, or ratios.

In certain embodiments, the methods provide for treating Prader-Willi Syndrome (PWS) comprising administering a phosphodiesterase 4 inhibitor (PDE4i) to a subject in need thereof, thereby alleviating, eliminating or preventing one or more symptoms of PWS.

In certain embodiments, administering the PDE4i upregulates cyclic adenosine monophosphate (cAMP) concentrations or activity in the subject.

In certain embodiments, PWS is characterized by decreased expression of NHLH2.

In additional embodiments, decreased expression of NHLH2 results in decreased expression of PCSK1.

In certain embodiments, increasing concentrations or activity of cAMP upregulates expression of Pcsk1.

In additional embodiments, the PDE4i is a selective PDE4i. In additional embodiments, the PDE4i is a non-selective PDE4i.

In certain embodiments, the selective PDE4i is selected from AN2728, apremilast, cilomilast, diazepam, ibudilast, luteolin, mesembrenone, piclamilast, roflumilast, rolipram, E6005, GSK356278 and MK0952.

In certain embodiments, the non-selective PDE4i selected from methylated xanthines and derivatives thereof, caffeine, aminophylline, 3-isobutyl-1-methylxanthine, paraxanthine, pentoxifylline, theobromine, and theophylline.

In yet additional embodiments, the one or more symptoms include hyperphagia, reduced metabolic rate, obesity, hypogonadism, hypoadrenalism, decreased growth hormone production, poor muscle tone, sleep disorders, gastrointestinal disorders, reduced stamina, reduced ability to focus, impaired cognition, behavioral disorders, anxiety, growth failure, reduced conversion of immature hormones to mature and active forms, and diabetes mellitus and diabetes insipidus.

In certain embodiments, the method further comprises administering one or more additional therapeutic agents effective for treating or alleviating one or more symptoms of PWS.

In certain embodiments, the immature hormones comprise one or more of insulin, ghrelin, GHRH, alpha-MSH, oxytocin, orexin, BDNF, vasopressin, NPY, AGRP, and gonadotropins, ACTH.

In certain embodiments, the one or more additional therapeutic agents effective at treating or alleviating PWS include insulin, an insulin receptor agonist, ghrelin, a ghrelin receptor agonist, GHRH, a GHRH receptor agonist, alpha-MSH, an alpha-MSH receptor agonist, oxytocin, an oxytocin receptor agonist, orexin, an orexin receptor agonist, BDNF, a BDNF receptor agonist, vasopressin, a vasopressin receptor agonist, NPY, an NPY receptor agonist, AGRP, an AGRP receptor agonist, gonadotropin, a gonadotropin receptor against, or combinations thereof.

BRIEF DESCRIPTION OF THE DRAWINGS

FIG. 6A: Theophylline increases PCSK1 transcript levels in D34 iPSC-derived hypothalamic ARC neurons (1023A line) at 10 mM concentration. FIGS. 6B-C: Roflumilast increases PCSK1 transcript levels in iPSC-derived neurons at Day 40 of differentiation (1043D3 line) at 1 mM concentration. FIGS. 6D-E: Combination treatment with Roflumilast (100 nM) and Forskolin (1 μM) increase PCSK1 transcript levels and increase POMC processing to ACTH at lower concentrations than either agent alone, suggesting an additive or possibly synergistic effect. FIG. 6F: MK0952 applied at 10 μM in combination with 1 μM Forskolin increases PCSK1 transcript levels ~2-fold in iPSC-derived neurons (1043D3 line).

FIG. 7A is a graph showing that body weights of all mice used were comparable. FIG. 7B is a graph showing that MK0952 administered by oral gavage in 10% methyl cellulose at a dose of 10 mg/kg body weight increased hypothalamic Pcsk1 levels by about 25%. Treatment with Forskolin at 25 mg/kg did not result in increased hypothalamic Pcsk1 levels. Combination treatment with MK0952 (10 mg/kg) and Forskolin (25 mg/kg) also resulted in a 25% increase in hypothalamic Pcsk1 transcript levels, likely due largely to the effects of MK0952.

FIGS. 8A-C are schematics, tables and graphs showing aspects of the clinical trial design.

DETAILED DESCRIPTION

Figure 1:
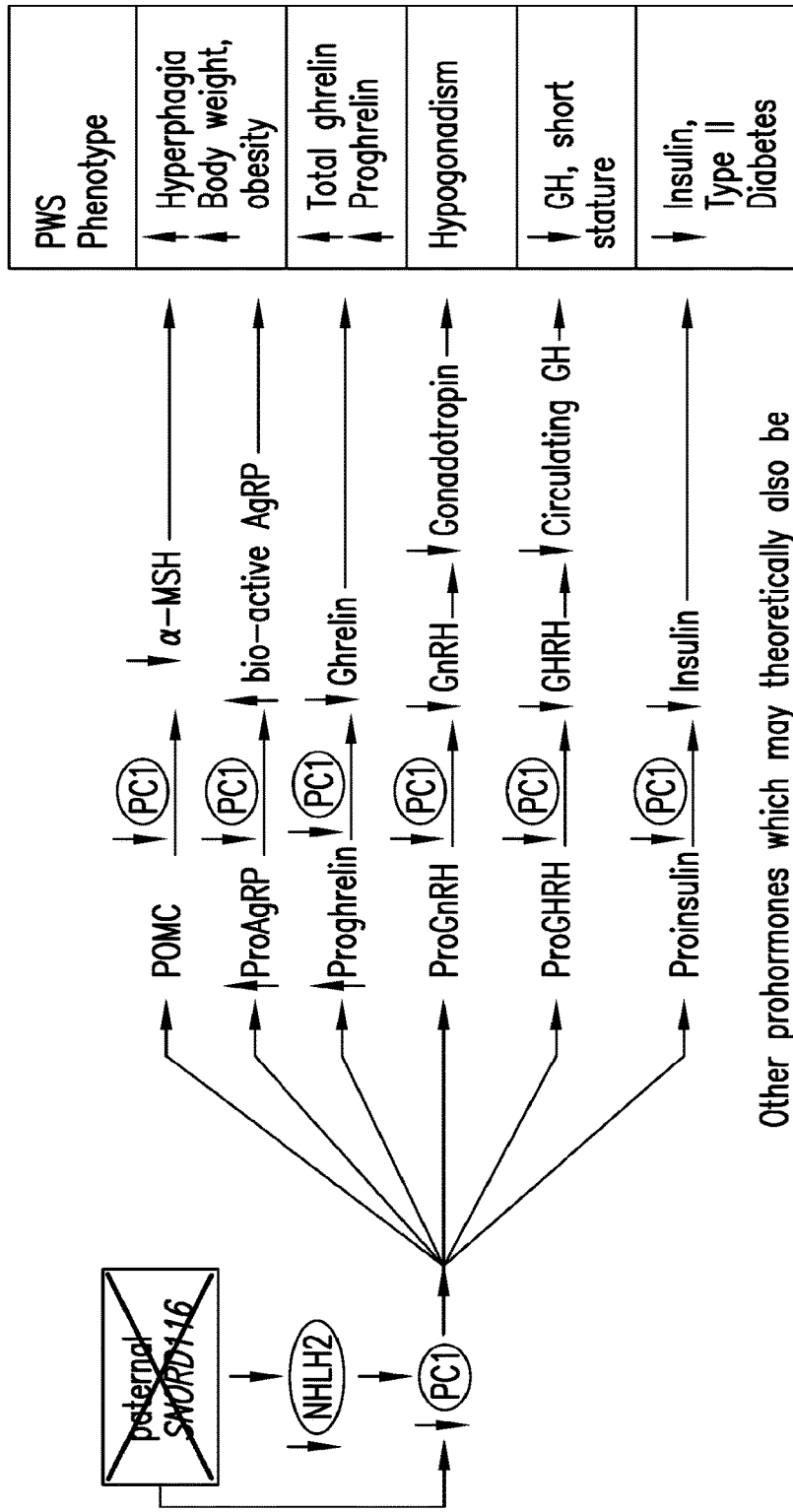
FIG. 1 is a model showing how deficiencies in Nhlh2 and PC1 may drive the major neuroendocrine phenotypes of PWS. A deficiency in prohormone processing owing to deficits in PC1 and Nhlh2 production may explain many of the major neuroendocrine phenotypes of PWS. It is hypothesized that paternal loss of SNORD116 may be sufficient to cause deficiencies in Nhlh2 and PC1, in turn causing functional defects in prohormone processing. Arrows/lines that are dashed indicate theoretical connections. Arrows/lines that are solid indicate pathways that have been investigated.

The present disclosure provides for methods to regulate PC1 (prohormone convertase 1) levels in vitro or in vivo. The methods can be used to upregulate (increase expression) or increase PC1 levels and/or activity. Also encompassed by the present disclosure are methods to treat Prader-Willi syndrome (PWS) and other forms of obesity. The methods may comprise the step of administering a therapeutically effective amount of a PDE4 inhibitor and/or an adenylate cyclase activator. It is also expected that these methods will be useful for treating patients with Schaaf-Yang Syndrome and Autism Spectrum Disorder (Fabienne Schaller Françoise Watrin Rachel Sturny Annick Massacrier Pierre Szepetowski Françoise Muscatelli; Hum Mol Genet (2010) 19 (24): 4895-4905. Green L, Fein D, Modahl C, Feinstein C, Waterhouse L, Morris M. Oxytocin and autistic disorder: alterations in peptide forms. Biol Psychiatry. 2001 Oct. 15; 50(8):609-13.

Theoretical mechanisms to increase cellular prohormone convertase 1 levels/activity include but are not limited to: (1) upregulation at the transcript level by engaging endogenous promoters, (2) directly increasing enzymatic activity of PC1, (3) increasing rates of translation of PCSK1 to PC1, (4) decreasing degradation of PC1 enzyme/protein, one possible approach is by decreasing levels (via antisense oligo "genetic knockdown," traditional small molecule inhibition, or other) of the endogenous inhibitor of PC1, ProSAAS, (5) decreasing degradation (miRNA targeted, non-sense mediated decay, putative mRNA methylation levels) of PCSK1 transcript, thereby increasing translation, (6) PC1 itself is processed from a 92 kDa zymogen to a 66 kDa mature enzyme, thus increasing levels of preproPC1 processing could also have therapeutic utility, and (7) delivery of additional PCSK1 cDNA to the cell by gene therapy methods, (8) delivery of SNORD116 RNAs by gene therapy methods, and (9) direct delivery of the PC1 enzyme into the circulation and/or tissues with enzyme replacement therapies.

The present findings suggest that the major neuroendocrine features of PWS are likely due to functional PC1 deficiency. See FIG. 1. As the gene encoding PC1, PCSK1, is intact in PWS, increasing the levels of PC1 expression and/or activity in PWS patients will correct this functional PC1 deficiency. Pharmacologically, this increase in PC1 levels can be achieved by administration of agents that increase cyclic adenosine monophosphate (cAMP) levels or block cAMP degradation.

Cyclic nucleotide phosphodiesterases (PDEs) catalyze the hydrolysis of cyclic AMP and cyclic GMP, thereby regulating the intracellular concentrations of these cyclic nucleotides, their signaling pathways and, consequently, a myriad of biological responses in health and disease. Maurice et al. Advances in targeting cyclic nucleotide phosphodiesterases. Nat. Rev. Drug. Discov. 13(4):290-314 (2014). PDE4 isoforms are highly expressed in cells that regulate immunoinflammatory responses and tissue remodeling. Id. Inhibition of PDE4 results in an increase in cAMP levels in the cell. A large number of PDE4 inhibitors are available. Non-limiting examples of PDE4 Inhibitors include: Theophylline, Roflumilast, Apremilast, Ibudilast, GSK356278, MK0952, IBMX (3-isobutyl-1-methylxanthine), Mesembrenone, Rolipram, Piclamilast, Luteolin, Drotaverine, AN2728, Cilomilast, Diazepam, Luteolin, and E6005. Other phosphodiesterase inhibitors include, methylated xanthines and derivatives (such as caffeine, aminophylline, paraxanthine, pentoxifylline, theobromine, and theophylline).

The levels of cAMP may also be increased using agents which activate adenylate cyclase. Non-limiting examples of adenylate cyclase activators include: Forskolin, FD1, FD2, FD3, FD4, FD5 (NKH477), and FD6.

PDE4 inhibitors and adenylate cyclase activators can be referred to alone or in combination as therapeutic agents.

TABLE 1A

Selected PDE4 Inhibitors

| Drug | PDE4 selectivity | Brain penetration | Status |
|---|---|---|---|
| Theophylline | nonselective | Good | Generic |
| Roflumilast | Selective | limited | Approved COPD: Takeda/AstraZeneca (LOE: 2020/2031) |
| Apremilast | Selective | None | approved psoriasis: Celgene (LOE: 2028) |
| Ibudilast | nonselective | Yes | approved in Japan Phase 2 2015 ALS by Medicinova in US |
| GSK356278 | Selective | Good | suspended: GSK Phase 1 2012 Huntington's Disease |
| MK0952 | selective | yes | suspended: Merck Phase 2 2007 Alzheimer's Disease; See: Heckman P R, Wouters C, Prickaerts J. Phosphodiesterase inhibitors as a target for cognition enhancement in aging and Alzheimer's disease: a translational overview. Curr Pharm Des. 2015; 21(3): 317-31. Review. PubMed PMID: 25159073. Gallant M, et al. Discovery of MK-0952, a selective PDE4 inhibitor for the treatment of long-term memory loss and mild cognitive impairment. Bioorg Med Chem Lett. 2010 Nov. 15; 20(22): 6387-93. doi: 10.1016/j.bmcl.2010.09.087. Epub 2010 Sep. 21. PubMed PMID: 20933411. |
| IBMX | nonselective | n/a | laboratory use only |

TABLE 1B

Compounds useful as PDE Inhibitors (PDEi)

| | | |
|---|---|---|
| GEBR-32a | AVE 8112A | BAY 60-7550 |
| Rolipram | GRC-4039 | Anagrelide |
| GEBR-7b | Revamilast | Cilostazol |
| Selaginpulvilins K | DG 071 | Milrinone |
| Selaginpulvilins L | MEM 1414 | Olprinone |
| GSK256066 | Mesopram | Parogrelil |
| Chlorbipram | SH 636 | Pimobendan |
| FFPM | ZK 117137 | Ibudilastroflumilast |
| Cilomilast | MEM-1018 | Ro 20-1724 |
| Piclamilast | MEM-1091 | CDP840 |
| BC8-15 | MEM-1917 | Tofimilast |
| ZL-n-91 | R 1627 | Oglemilast |
| NIS-62949 | AV-11 | Tetomilast |

TABLE 1B-continued

Compounds useful as PDE Inhibitors (PDEi)

| | | |
|---|---|---|
| CHF6001 | AV-411 | Lirimifast |
| 4-(8-(3-Fluorophenyl)-1,7-naphthyridin-6-yl)transcyclohexanecarboxylic Acid | Eyevinal | Sildenafil |
| 4,5,6,7-tetrahydro-1H-1,2-diazepin-7-one derivatives | Ibinal | Tadalafil |
| PDE-310 | KC-404 | Vardenafil |
| RPL554 | Ketas | Udenafil |
| L-454,560 | MN-166 | Avanafil |
| GS-5759 | Pinatos | Dipyridamole |
| BPN14770 | D159687 | E-4010 |
| TAK-648 | D159797 | E-4021 |
| PF-02545920 | BPN14770 | E-8010 |
| RO5545965 | PF-00489791 | Zaprinast |
| AMG 579 | PF-04447943 | Iodenafil |
| TAK 063 | ABI-4 | Mirodenafil |
| PF-05180999 | Crisaborole | DA-8159 |
| BCA909 | FCPR03 | BAY 73-6691 |
| HT-0712 | A-33 | PF-2545920 |
| Ro-20-1724 | T-094 | SCH-1518291 |
| ME 3167 | Resveratrol | 4-amino substituted condensed pyrimidine compounds as PDE4 inhibitors (See: U.S. Pat. No. 9,505,724 B2) |
| ZK 62711 | ITI-214 | Substituted pyridine and pyrazine compounds as PDE4 inhibitors (See U.S. Pat. No. 9,573,937 B2) |
| APTA-2217 | Cilostazol | Azabenzimidazole compounds (See U.S. Pat. No. 9,120,788 B2) |
| B 9302-107 | Milrinone | phosphodiesterase type 4 inhibitors, containing 2-phenyl-4-oxazole moiety, exemplified by "compound 4C" from Li Y S et al Design, synthesis and biological evaluation of 2,4-disubstituted oxazole derivatives as potential PDE4 inhibitors. Bioorg Med Chem. 2017 Mar. 15; 25(6): 1852-1859. doi: 10.1016/j.bmc.2017.01.047. Epub 2017 Feb. 3. |
| BY 217 | Enoximone | Heteroaryl inhibitors of PDE4 - as described in: WO2015048407A1. |
| BYK 20869 | ASP9831 | |
| Daliresp | Tadalafil | |
| Daxas | Sildenafil | |
| IN-ALR 01 | AN2898 | |
| Libertek | AN2728 | |
| DNS 001 | vinpocetine | |
| AVE 8112 | erythro-9-(2-hydroxy-3-nonyl)adenine (EHNA) | |

TABLE 2

Selected Adenylate Cyclase Activators

| Drug | AC isoforms activated | Brain penetration | Status |
|---|---|---|---|
| Forskolin | All except AC9 | Yes | OTC |
| FD1 | AC2 (AC2 expressed in brain, skeletal muscle, lung, heart [7]) | Not tested | Synthesized by Nippon Kayaku Co. only tested in cell-based models, not FDA-approved |
| FD2 | AC2 | Not tested | Synthesized by Nippon Kayaku Co. only tested in cell-based models, not FDA-approved |
| FD3 | AC3 (AC3 expressed in brain, olfactory, epithelium [7]) | Not tested | Synthesized by Nippon Kayaku Co. only tested in cell-based models, not FDA-approved |
| FD4 | AC3 | Not tested | Synthesized by Nippon Kayaku Co. only tested in cell-based models, not FDA-approved |

TABLE 2-continued

Selected Adenylate Cyclase Activators

| Drug | AC isoforms activated | Brain penetration | Status |
|---|---|---|---|
| FD5 (NKH477) | AC5 (AC5 expressed in heart, brain, kidney, liver, lung, uterus, adrenal, brown adipose tissue [7]) | Not tested | Synthesized by Nippon Kayaku Co. only tested in cell-based models, not FDA-approved |
| FD6 | AC5 | Not tested | Synthesized by Nippon Kayaku Co. only tested in cell-based models, not FDA-approved |

Abbreviations

ACTH: adrenocorticotropic hormone.

AgRP: Agouti-related protein; a protein also produced in the arcuate nucleus and is an inverse agonist at MC4R. ProAgRP is processed to AgRP by PC1.

cAMP: cyclic adenosine monophosphate

GH: Ghrelin (the "hunger hormone", also known as lenomorelin (INN), is a peptide hormone produced by enteroendocrine cells in the fundus of the stomach which functions as a neuropeptide in the central nervous system.

proGHRH: progrowth hormone-releasing hormone.

GHRH: Growth hormone-releasing hormone (GHRH), also known as somatoliberin or by several other names in its endogenous forms and as somatorelin (INN) in its pharmaceutical form, is a releasing hormone of growth hormone (GH). It is a 44-amino acid peptide hormone produced in the arcuate nucleus of the hypothalamus.

PC1: Proprotein convertase 1, also known as prohormone convertase 1, prohormone convertase 3, proprotein convertase 3, neuroendocrine convertase 1, or neuroendocrine convertase 3, and often abbreviated as PC1/3 is an enzyme that in humans is encoded by the PCSK1 gene. PC1 and PC2, the protein products of the PCSK1 and PCSK2 genes, differentially cleave many neuroendocrine or endocrine hormones, including, proopiomelanocortin, proinsulin, and proglucagon.

PC2: Proprotein convertase 2 (PC2) also known as prohormone convertase 2 or neuroendocrine convertase 2 (NEC2) is a serine protease and proprotein convertase PC2, like proprotein convertase 1 (PC1), is an enzyme responsible for the first step in the maturation of many neuroendocrine peptides from their precursors, such as the conversion of proinsulin to insulin intermediates. To generate the bioactive form of insulin (and many other peptides), a second step involving the removal of C-terminal basic residues is required; this step is mediated by carboxypeptidases E and/or D. PC2 plays only a minor role in the first step of insulin biosynthesis, but a greater role in the first step of glucagon biosynthesis compared to PC1. PC2 binds to the neuroendocrine protein named 7B2, and if this protein is not present, proPC2 cannot become enzymatically active. 7B2 accomplishes this by preventing the aggregation of proPC2 to inactivatable forms. The C-terminal domain of 7B2 also inhibits PC2 activity until it is cleaved into smaller inactive forms. Thus, 7B2 is both an activator and an inhibitor of PC2. In humans, proprotein convertase 2 is encoded by the PCSK2 gene. It is related to the bacterial enzyme subtilisin, and altogether there are 9 different subtilisin-like genes in mammals: furin, PACE4, PC4, PC5/6, PC7/8, PCSK9, and SKI1/S1P.

PCSK1: the gene encoding PC1.

PCSK2: the gene encoding PC2.

POMC: Pro-opiomelanocortin (POMC) is a precursor polypeptide with 241 amino acid residues. POMC is synthesized in the pituitary from the 285-amino-acid-long polypeptide precursor pre-pro-opiomelanocortin (pre-POMC), by the removal of a 44-amino-acid-long signal peptide sequence during translation.

PDE4: phosphodiesterase 4.

PWS: Prader Willi Syndrome.

SNORD 116: SNORD116 (also known as HBII-85) is a non-coding RNA (ncRNA) molecule which functions in the modification of other small nuclear RNAs (snRNAs). This type of modifying RNA is usually located in the nucleolus of the eukaryotic cell which is a major site of snRNA biogenesis. It is known as a small nucleolar RNA (snoRNA) and also often referred to as a guide RNA. SNORD116 belongs to the C/D box class of snoRNAs which contain the conserved sequence motifs known as the C box (UGAUGA) and the D box (CUGA). Most of the members of the box C/D family function in directing site-specific 2'-O-methylation of substrate RNAs. In the human genome, there are 29 tandemly repeated copies of SNORD116, in the PWS region of chromosome 15. In addition, other non-coding RNA species are encoding from the SNORD116 locus, including the long noncoding RNA, 116HG, five sno-lncRNAs, and two spa-lncRNAs. SNORD116 is an orphan non-coding RNA locus that lacks clearly defined targets. Mouse models lacking paternal Snord116 show similar symptoms to human PWS including hyperphagia and growth deficiency.

DPI devices/inhalers: dry powder inhalers; typically hand-held.

MDI devices: metered-dose inhalers; typically hand-held.

αMSH: is an endogenous ligand of the melanocortin 4 receptor.

MC2R: melanocortin 2 receptor.

MC4R: melanocortin 4 receptor.

WT: wildtype.

Definitions

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent. The diluent or carrier ingredients should not be such as to diminish the therapeutic effects of the active compound(s).

The term "composition" as used herein means a product which results from the mixing or combining of more than one element or ingredient.

"Treating" or "treatment" of a state, disorder or condition includes:

(1) preventing or delaying the appearance of clinical symptoms of the state, disorder, or condition developing in a person who may be afflicted with or predisposed to the state, disorder or condition but does not yet experience or display clinical symptoms of the state, disorder or condition; or (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease, i.e., causing regression of the state, disorder or condition or at least one of its clinical or sub-clinical symptoms or signs.

The benefit to a subject to be treated is either statistically significant or at least perceptible to the patient or to the physician.

"Patient" or "subject" refers to mammals and includes human and veterinary subjects.

"Inhibitors" and "antagonists," or "activators" and "agonists," refer to inhibitory or activating molecules, respectively, e.g., for the activation of, e.g., a ligand, receptor, cofactor, a gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule. Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a compound that reduces, blocks, or inactivates a constitutive activity. An "agonist" is a compound that interacts with a target to cause or promote an increase in the activation of the target. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activator or inhibitor and are compared to control samples without the inhibitor. Control samples, i.e., samples not treated with antagonist, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

The dosage of the therapeutic formulation will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. In some cases, oral administration will require a higher dose than if administered intravenously. In some cases, topical administration will include application several times a day, as needed, for a number of days or weeks in order to provide an effective topical dose.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, olive oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Therapeutic compositions described herein may be administered by any method known in the art, including, without limitation, intranasal, oral, transdermal, ocular, intraperitoneal, inhalation, intravenous, ICV, intracisternal injection or infusion, subcutaneous, implant, vaginal, sub-lingual, urethral (e.g., urethral suppository), subcutaneous, intramuscular, intravenous, rectal, sub-lingual, mucosal, ophthalmic, spinal, intrathecal, intra-articular, intra-arterial, sub-arachinoid, bronchial or lymphatic administration. Topical formulation may be in the form of gel, ointment, cream, aerosol, etc.; intranasal formulation can be delivered as a spray or in a drop; transdermal formulation may be administered via a transdermal patch or iontophoresis; or, inhalation formulations can be delivered using a nebulizer or similar device. Compositions can also take the form of tablets, pills, capsules, semisolids, powders, sustained release formulations, solutions, suspensions, elixirs, aerosols, or any other appropriate compositions.

To prepare such pharmaceutical compositions, one or more PDE4 inhibitors and/or one or more adenylate cyclase activators, and/or one or more MC4R agonists may be mixed together with a pharmaceutical acceptable carrier, adjuvant and/or excipient, according to conventional pharmaceutical compounding techniques. Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers and adjuvants, see *Remington's Pharmaceutical Sciences*, edited by E. W. Martin (Mack Publishing Company, 18th ed., 1990). The compositions also can include stabilizers and preservatives.

As used herein, the term a "therapeutically effective amount" is an amount sufficient to treat a specified disorder or disease or alternatively to obtain a pharmacological response treating a disorder or disease in vitro or in vivo in a mammal such as a human or non-human patient. Methods of determining the most effective means and dosage of administration can vary with the composition used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. Suitable dosage formulations and methods of administering the agents can be readily determined by those of skill in the art. For example, the composition is administered at about 0.01 mg/kg to about 200 mg/kg, about 0.1 mg/kg to about 100 mg/kg, or about 0.5 mg/kg to about 50 mg/kg. When the compounds described herein are co-administered with another agent or therapy, the effective amount may be less than, equal to or greater than when either agent is used alone.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer. If the composition is in the form of a gel, the composition may be rubbed onto a membrane of the patient, for example, the skin, preferably intact, clean, and dry skin, of the shoulder or upper arm and or the upper torso, and maintained thereon for a period of time sufficient for delivery of the PDE4 inhibitor and/or the adenylate cyclase activator to the blood serum of the patient. The composition of the present invention in gel form may be contained in a tube, a sachet, or a metered pump. Such a tube or sachet may contain one unit dose, or more than one unit dose, of the composition. A metered pump may be capable of dispensing one metered dose of the composition.

This invention also provides the compositions as described above for intranasal administration. As such, the compositions can further comprise a permeation enhancer. Southall et al. *Developments in Nasal Drug Delivery,* 2000. The PDE4 inhibitor and/or the adenylate cyclase activator may be administered intranasally in a liquid form such as a solution, an emulsion, a suspension, drops, or in a solid form such as a powder, gel, or ointment. Devices to deliver intranasal medications are well known in the art. Nasal drug delivery can be carried out using devices including, but not limited to, intranasal inhalers, intranasal spray devices, atomizers, nasal spray bottles, unit dose containers, pumps, droppers, squeeze bottles, nebulizers, metered dose inhalers (MDI), pressurized dose inhalers, insufflators, and bi-directional devices. The nasal delivery device can be metered to administer an accurate effective dosage amount to the nasal cavity. The nasal delivery device can be for single unit delivery or multiple unit delivery. In a specific example, the ViaNase Electronic Atomizer from Kurve Technology (Bethell, Washington) can be used in this invention (http://www.kurvetech.com). The compounds of the present invention may also be delivered through a tube, a catheter, a syringe, a packtail, a pledget, a nasal tampon or by submucosal infusion. U.S. Patent Publication Nos. 20090326275, 20090291894, 20090281522 and 20090317377.

The PDE4 inhibitor and/or the adenylate cyclase activator can be formulated as aerosols using standard procedures. The PDE4 inhibitor and/or the adenylate cyclase activator may be formulated with or without solvents, and formulated with or without carriers. The formulation may be a solution, or may be an aqueous emulsion with one or more surfactants. For example, an aerosol spray may be generated from pressurized container with a suitable propellant such as, dichlorodifluoromethane, trichlorofluoromethane, dichlorotetrafluoroethane, hydrocarbons, compressed air, nitrogen, carbon dioxide, or other suitable gas. The dosage unit can be determined by providing a valve to deliver a metered amount. Pump spray dispensers can dispense a metered dose or a dose having a specific particle or droplet size. As used herein, the term "aerosol" refers to a suspension of fine solid particles or liquid solution droplets in a gas. Specifically, aerosol includes a gas-borne suspension of droplets of a PDE4 inhibitor and/or the adenylate cyclase activator as may be produced in any suitable device, such as an MDI, a nebulizer, or a mist sprayer. Aerosol also includes a dry powder composition of the composition of the instant invention suspended in air or other carrier gas. Gonda (1990) *Critical Reviews in Therapeutic Drug Carrier Systems* 6:273-313. Raeburn et al., (1992) *Pharmacol. Toxicol. Methods* 27:143-159.

The PDE4 inhibitor and/or the adenylate cyclase activator may be delivered to the nasal cavity as a powder in a form such as microspheres delivered by a nasal insufflator. The PDE4 inhibitor and/or the adenylate cyclase activator may be absorbed to a solid surface, for example, a carrier. The powder or microspheres may be administered in a dry, air-dispensable form. The powder or microspheres may be stored in a container of the insufflator. Alternatively, the powder or microspheres may be filled into a capsule, such as a gelatin capsule, or other single dose unit adapted for nasal administration.

The pharmaceutical composition can be delivered to the nasal cavity by direct placement of the composition in the nasal cavity, for example, in the form of a gel, an ointment, a nasal emulsion, a lotion, a cream, a nasal tampon, a dropper, or a bioadhesive strip. In certain embodiments, it can be desirable to prolong the residence time of the pharmaceutical composition in the nasal cavity, for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl).

The composition containing the PDE4 inhibitor and/or the adenylate cyclase activator can be administered by oral inhalation into the respiratory tract, i.e., the lungs.

Typical delivery systems for inhalable agents include nebulizer inhalers, dry powder inhalers (DPI), and metered-dose inhalers (MDI).

Nebulizer devices produce a stream of high velocity air that causes a therapeutic agent in the form of liquid to spray as a mist. The therapeutic agent is formulated in a liquid form such as a solution or a suspension of particles of suitable size. In one embodiment, the particles are micronized. The term "micronized" is defined as having about 90% or more of the particles with a diameter of less than about 10 µm. Suitable nebulizer devices are provided commercially, for example, by PARI GmbH (Starnberg, Germany). Other nebulizer devices include Respimat (Boehringer Ingelheim) and those disclosed in, for example, U.S. Pat. Nos. 7,568,480 and 6,123,068, and WO 97/12687. The PDE4 inhibitor and/or the adenylate cyclase activator can be formulated for use in a nebulizer device as an aqueous solution or as a liquid suspension.

DPI devices typically administer a therapeutic agent in the form of a free flowing powder that can be dispersed in a patient's air-stream during inspiration. DPI devices which use an external energy source may also be used in the present invention. In order to achieve a free flowing powder, the therapeutic agent can be formulated with a suitable excipient (e.g., lactose). A dry powder formulation can be made, for example, by combining dry lactose having a particle size between about 1 μm and 100 μm with micronized particles of the present compounds and dry blending. Alternatively, the present compounds can be formulated without excipients. The formulation is loaded into a dry powder dispenser, or into inhalation cartridges or capsules for use with a dry powder delivery device. Examples of DPI devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI devices typically discharge a measured amount of therapeutic agent using compressed propellant gas. Formulations for MDI administration include a solution or suspension of active ingredient in a liquefied propellant. Examples of propellants include hydrofluoroalklanes (HFA), such as 1,1,1,2-tetrafluoroethane (HFA 134a) and 1,1,1,2,3,3,3-heptafluoro-n-propane, (HFA 227), and chlorofluorocarbons, such as $CCl_3F$. Additional components of HFA formulations for MDI administration include co-solvents, such as ethanol, pentane, water; and surfactants, such as sorbitan trioleate, oleic acid, lecithin, and glycerin. (See, for example, U.S. Pat. No. 5,225,183, EP 0717987, and WO 92/22286). The formulation is loaded into an aerosol canister, which forms a portion of an MDI device. Examples of MDI devices developed specifically for use with HFA propellants are provided in U.S. Pat. Nos. 6,006,745 and 6,143,227. For examples of processes of preparing suitable formulations and devices suitable for inhalation dosing see U.S. Pat. Nos. 6,268,533, 5,983,956, 5,874,063, and 6,221,398, and WO 99/53901, WO 00/61108, WO 99/55319 and WO 00/30614.

The PDE4 inhibitor may be encapsulated in liposomes or microcapsules for delivery via inhalation. A liposome is a vesicle composed of a lipid bilayer membrane and an aqueous interior. The lipid membrane may be made of phospholipids, examples of which include phosphatidylcholine such as lecithin and lysolecithin; acidic phospholipids such as phosphatidylserine and phosphatidylglycerol; and sphingophospholipids such as phosphatidylethanolamine and sphingomyelin. Alternatively, cholesterol may be added. A microcapsule is a particle coated with a coating material. For example, the coating material may consist of a mixture of a film-forming polymer, a hydrophobic plasticizer, a surface activating agent or/and a lubricant nitrogen-containing polymer. U.S. Pat. Nos. 6,313,176 and 7,563,768.

The PDE4 inhibitor and/or the adenylate cyclase activator can be given alone or in combination with other drugs for the treatment of the above diseases for a short or prolonged period of time, e.g., 1, 2, 3, 4, 5, 6, 7, 8, 9, 10, 20, 30, 40, 50 or 60 days or 1, 2, 4, 5, 6, 7, 8, 9, 10, 11 or 12 months or continuously over the lifetime of the patient. The present compositions can be administered to a mammal, preferably a human patient. Mammals include, but are not limited to, mice, rats, rabbit, simians, bovines, ovine, porcine, canines, feline, farm animals, sport animals, pets, equine, and primates.

The following are non-limiting examples.

Example 1

Manipulation of PC1 Expression and Activity in iPSC-Derived Hypothalamic Neurons and β-Cells Cyclase activation by Forskolin and/or inhibition of cAMP catabolism by inhibition of phosphodiesterase (Theophylline, IBMX) will increase PC1 levels in in vitro models of PWS with consequential increases in prohormone processing. The identification of an apparent multi-tissue deficiency in PCSK1 in in vivo and in vitro models of PWS enables rational therapeutic targeting that may alleviate the major neuroendocrine symptoms of PWS (FIG. 1).

The promoter region of the PCSK1 gene contains two cyclic adenosine monophosphate (cAMP)-response elements (Conkright et al. 2003; Udupi et al. 1998). Agents that increase cellular levels of cAMP increase PCSK1 mRNA and increase the secretion of prohormones processed by PC1 (FIG. 2)(Udupi 1998). Forskolin and Theophylline are two FDA-approved drugs with generally safe treatment profiles in pediatric populations. Forskolin binds to adenylate cyclase close to its catalytic domain through hydrophobic interactions and hydrogen bonding (Tang and Hurley 1998, Tesmer et al. 1999). Forskolin binding causes adenylate cyclase conformation to change to its active form, thus increasing AC activity and increasing cellular cAMP levels (Onda et al 2001). Theophylline and other phosphodiesterase 4 (PDE4) inhibitors, such as MK0952, increase cellular cAMP levels by blocking its degradation.

Non-limiting examples of PDE4 inhibitors include Theophylline, MK0952, as well as the other PDE inhibitors in Tables 1A-B. Non-limiting examples of adenylate cyclase (AC) activators include Forskolin and the activators in Table 2.

Agents that can be used in the present method also include agents that can modify G protein activity, such as G protein activators or inhibitors, as well as G protein coupled receptor agonists.

Figure 3A:
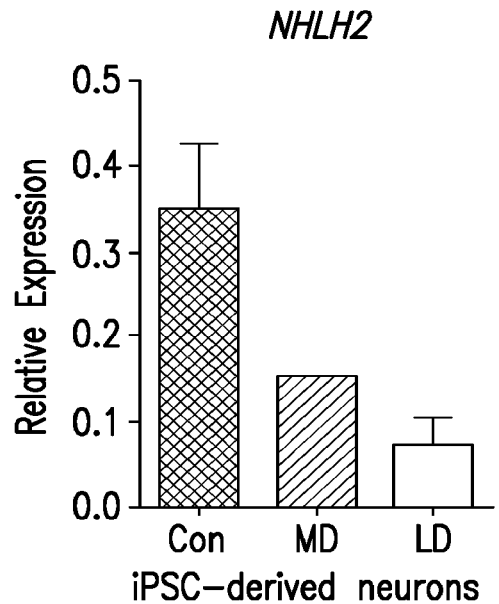
FIGS. 3A-P are graphs showing downregulation of PC1 in PWS models is associated with impaired prohormone processing; PCSK1 transcript levels can be increased in unaffected control by treatment with Forskolin.
Figure 3B:
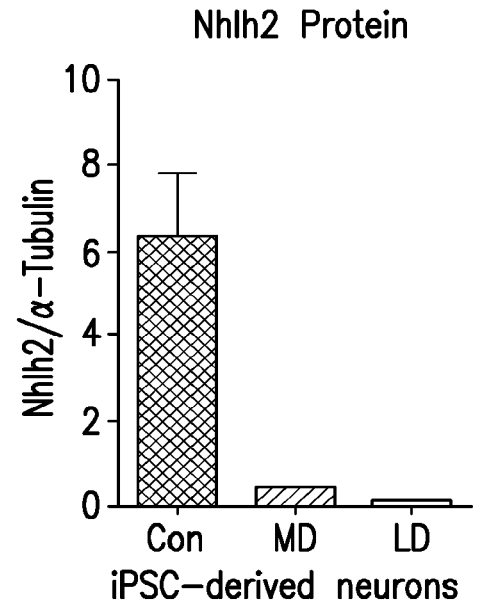
Figure 3C:
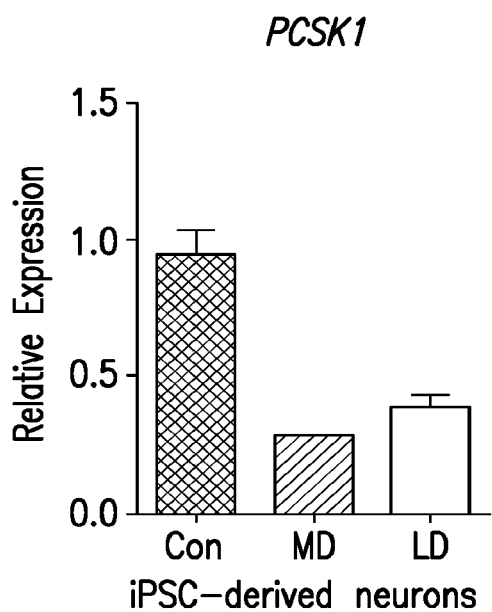
Figure 3D:
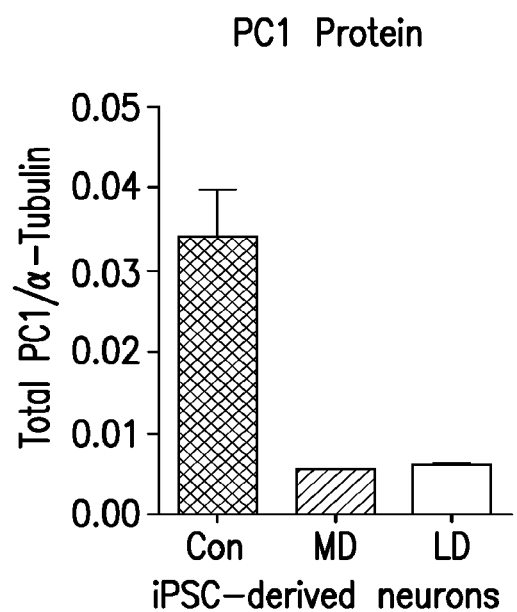
Figure 3E:
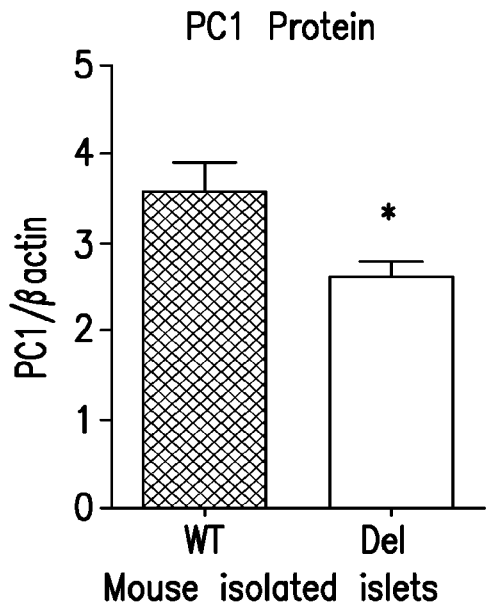
Figure 3F:
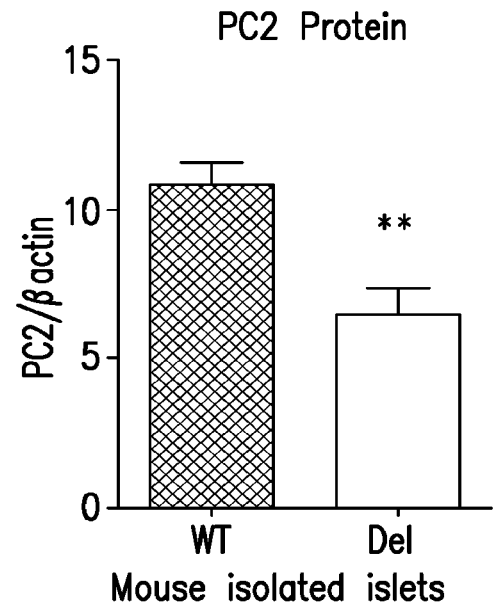
Figure 3G:
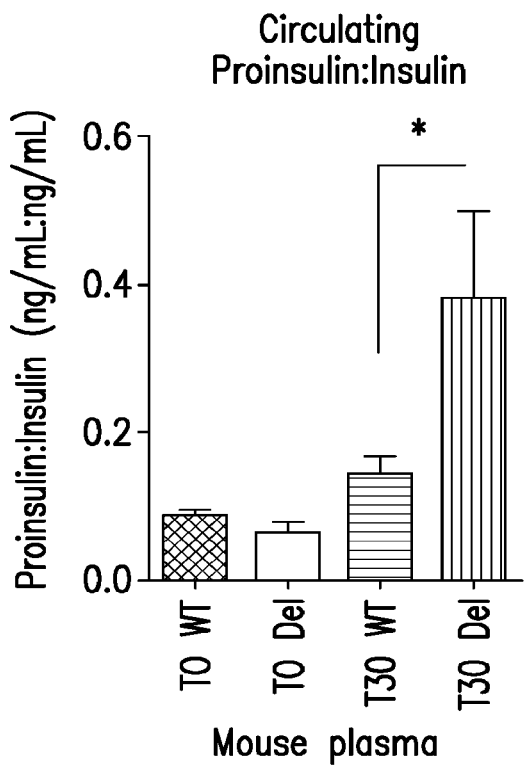
Figure 3H:
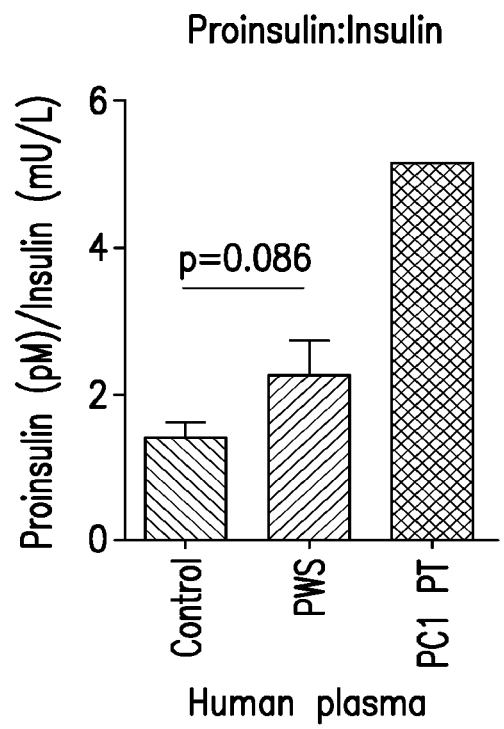
Figure 3I:
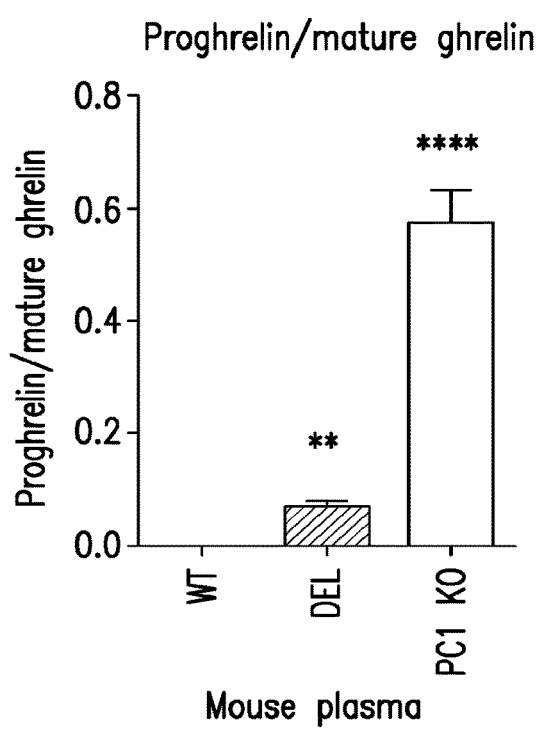
Figure 3J:
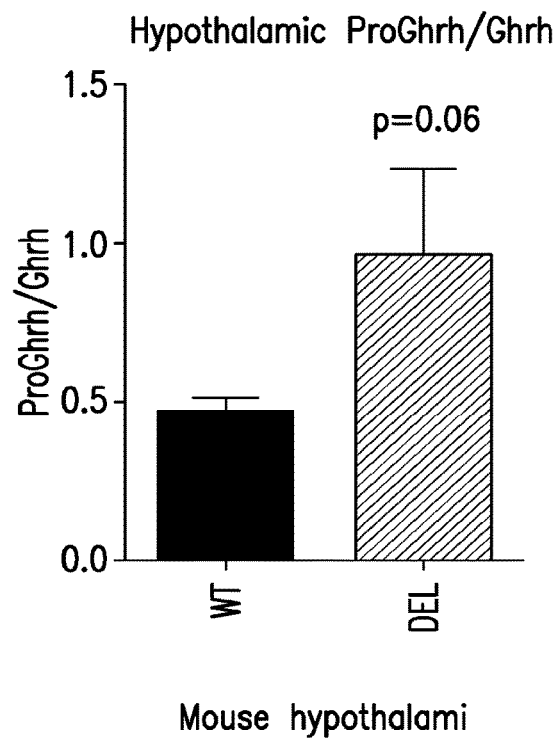
Figure 3K:
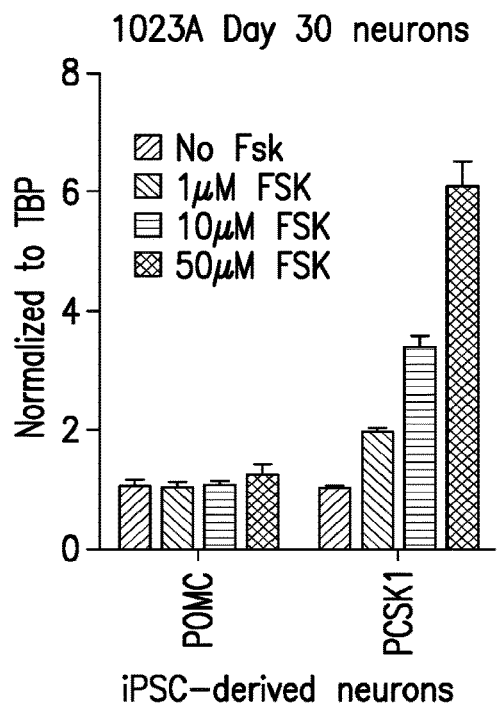
Figure 3L:
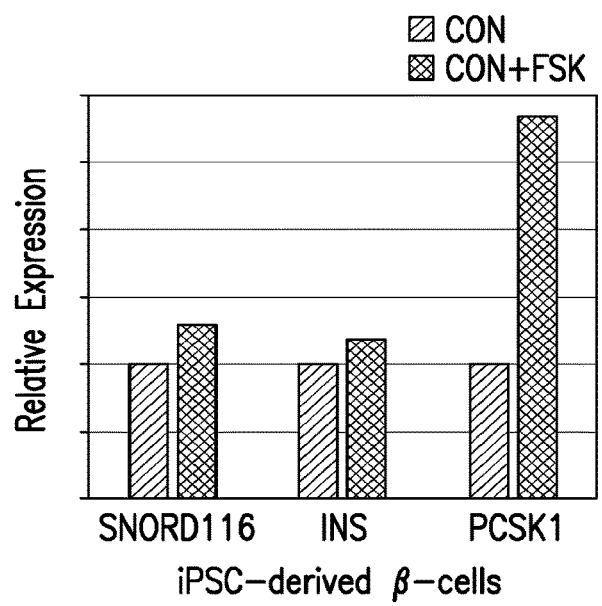
Figure 3M:
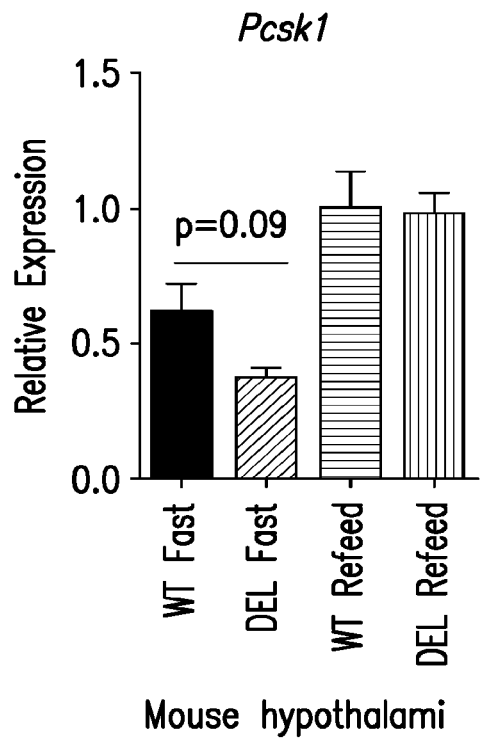
Figure 3N:
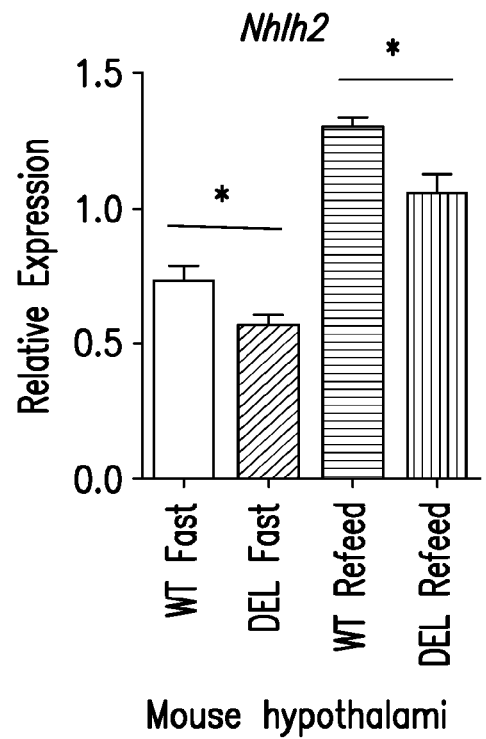
Figure 3O:
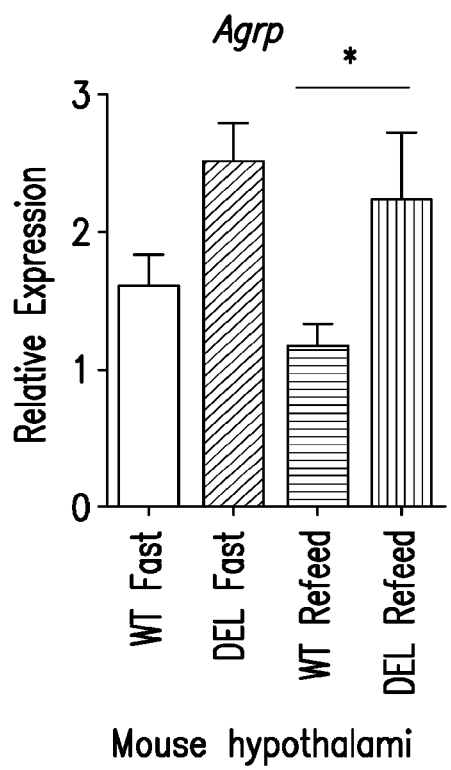
Figure 3P:
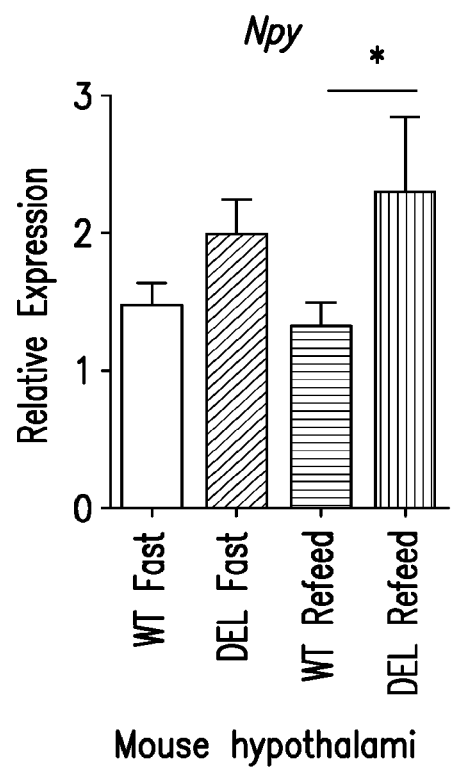

NHLH2 and PCSK1 are downregulated in PWS microdeletion and large deletion iPSC-derived neurons, as shown by RNA sequencing (FIGS. 3A, 3C). FIG. 3A: NHLH2 is downregulated in PWS microdeletion and large deletion iPSC-derived neurons compared to unaffected controls. FIG. 3B: NHLH2 protein is downregulated>90% in PWS microdeletion and large deletion iPSC-derived neurons compared to unaffected controls. FIGS. 3C-D: PCSK1 transcript and its protein product, PC1, are downregulated>55% and >80%, respectively in PWS microdeletion and large deletion iPSC-derived neurons compared to unaffected controls. FIGS. 3 E-F: Mice in which only the paternal copy of Snord116 has been deleted (rest of PWS region is intact) display>40% downregulation of PC1 and PC2 protein in isolated islets. FIG. 3G: Proinsulin is dependent on PC1 for its proper processing. There is a functional impairment in proinsulin processing in Snord116$^{p-/m+}$ mice compared to WT littermates at 30 minutes following glucose injection. FIG. 3H: There is 60% increase in the ratio of proinsulin to insulin in the plasma of individuals with PWS compared to age and BMI-matched controls at fasting, indicating a defect in proinsulin to insulin processing. The effect is less than that seen in a patient with a PC1 mutation, consistent with the ~50% reduction of PC1 in PWS models. FIG. 3I: Proghrelin is also processed by PC1; proghrelin processing is impaired in stomach lysates from Snord116$^{p-/m+}$ mice compared to WT littermates. Stomach lysates from PC1 null mice are included as a positive control for impaired proghrelin processing. FIG. 3J: ProGHRH processing may also be impaired in hypothalamic lysates from Snord116$^{p-/m+}$ mice compared to WT littermates, p=0.06. Impaired proGHRH processing is associated with low circulating GH and dwarfism in PC1 null mice. Snord116$^{p-/m+}$ also display low GH and severe runting. FIG. 3K: Preliminary data suggests that treatment of unaffected control hypothalamic iPSC-derived neurons with Forskolin (FSK) may increase transcript levels of PCSK1 in a dose-dependent manner. POMC transcript levels may not be affected. FIG. 3L: Treatment of unaffected control iPSC-derived β-cells with Forskolin increases PCSK1 transcript levels. SNORD116 and INS transcript levels may be minimally affected. FIG. 3M: Transcript levels of Pcsk1 are decreased 41% in Snord116p−/m+ hypothalamic at fasting; there is no difference in Pcsk1 levels at refeeding. FIG. 3N: Transcript levels of Nhlh2 are decreased at both fasting and after refeeding in Snord116p−/m+ hypothalamic compared to WT littermates. FIGS. 3O-P: Agrp and Npy transcript levels are increased in Snord116p−/m+ hypothalamic at refeeding compared to WT. Follow-up, independent experiments confirmed these changes by QPCR (gene expression) and Western blotting (protein level) (FIGS. 3B, 3D). Individuals with PWS exhibit decreased fasting insulin levels as compared to age and BMI matched controls. It was hypothesized that this may be due to impaired proinsulin processing. The present data illustrates that in a mouse model of PWS, in which only the paternal copy of Snord116 is deleted, PC1 and PC2 protein levels are decreased in isolated islets and are associated with a functional impairment in the processing of proinsulin to insulin (FIGS. 3E-3G). Proinsulin processing is also impaired (p=0.089) in plasma from human PWS patients compared to age, BMI-matched controls at fasting (FIG. 3H). Plasma from a fasted patient harboring a PC1 mutation was included as a positive control for impaired proinsulin processing.

The hyperghrelinemia of PWS patients is a unique phenotype that may be associated with impaired processing of proghrelin to mature ghrelin. Indeed, the present results illustrate that proghrelin to mature ghrelin processing was impaired in stomach lysates of Snord116$^{p-/m+}$ mice compared to WT littermates (FIG. 3I). Stomach lysates from PC1 null mice were included as a positive control for impaired proghrelin processing.

Like individuals with PWS, patients with PC1 mutation have decreased circulating GH levels. Mice null for PC1 have severe runting and decreased circulating GH associated with impaired proGHRH to GHRH processing. We found that Snord116$^{p-/m+}$ mice, which are also runted and have low circulating GH, trend towards impaired processing of proGHRH to GHRH in hypothalamic lysates (FIG. 3J).

Figure 2:
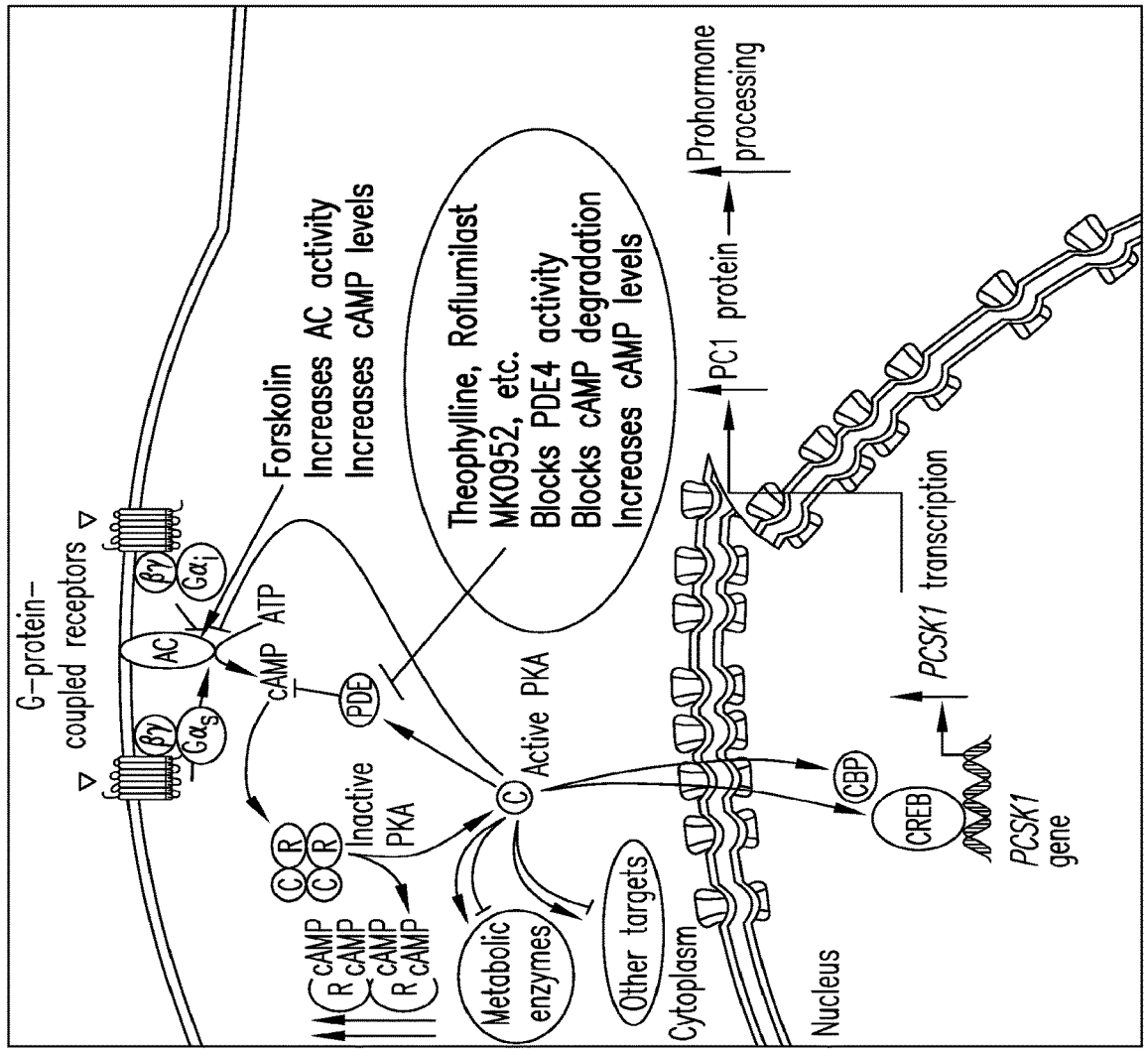
FIG. 2 is a schematic showing the rationale for treatment of PWS utilizing agents that increase cellular cAMP levels in order to increase level and/or activity of cellular PC1 and increase prohormone processing.

As outlined in FIG. 2, the identification of a decrease in PC1 and impaired prohormone processing in PWS suggests a unified molecular theory which may account for many of the neuroendocrine features of the disease. Thus, agents that increase PC1 activity and thereby increase prohormone processing, represent a rational, targeted therapy for the major neuroendocrine features of PWS.

Forskolin is known to increase cellular Pcsk1 levels and can increase prohormone processing. Forskolin was applied to non-PWS iPSC-derived neurons and β-cells and the results illustrate that PCSK1 transcript levels increased compared to untreated cells (FIGS. 3K-L). Studies in PWS-derived neurons and β-cells will be conducted.

The response of PCSK1 transcript levels, PC1 protein levels, and relevant prohormone processing levels will be tested in in vitro and in vivo model systems. We will treat unaffected control and hypothalamic iPSC-derived neurons with graded levels of Forskolin, Theophylline, and Forskolin+Theophylline and measure PC1 transcript and protein, POMC transcript and protein, as well as protein levels of processed products of POMC including: αMSH, β-endorphin, and ACTH. These peptides will be quantitated in whole cell lysates as well as the levels secreted into the cellular medium. The cells will be treated with different concentrations of Forskolin and Theophylline in order to determine whether PC1 levels can be increased in a dose-dependent manner and in order to identify an optimal dosage range to increase PC1 levels and POMC processing. Other PDE4 and adenylate cyclase inhibitors will be tested in these assays as well (see, Tables 1A-B and 2).

Batch RNA sequencing and/or single cell RNA sequencing will be performed to identify other transcripts that are most affected by the pharmacological treatments. This approach is expected to predict off-target effects upon in vivo treatment. Single cell RNA sequencing will be especially informative regarding PCSK1 transcript increases following treatment in POMC-expressing neurons. Other adenylate cyclase activators and PDE4 inhibitors (Tables 1A-B, 2) will be tested in iPSC-derived hypothalamic neurons following the same study protocol as described above.

We will differentiate iPSC from unaffected control and PWS (large and minimum deletion) to iPSC-derived β-cells. We will treat the iPSC-derived β-cells with Forskolin, Theophylline, and Forskolin+Theophylline and measure levels of PC1 at the transcript and protein level. We will also measure INS transcript levels as well as protein levels of proinsulin, insulin, and c-peptide from whole cell lysates as well as the concentrations of the proteins secreted by the β-cells into the media. These cells may be transplanted into nude mice to enable their maturation; these cells can be tested in vivo for insulin processing; excised cells will be tested as described. We will also use human isolated islets from non-diabetic, non-obese individuals (available to us through the National Pancreatic Donors Registry) to test the effects of Forskolin, Theophylline, and Forskolin+Theophylline on PC1 levels in fully mature human pancreatic islets.

Example 2

Confirmatory molecular physiology of PC1 metabolism in Snord116$^{p-/m+}$, Pc1$^{-/-}$ and Pc1$^{+/-}$ Mice.

Increasing cAMP levels by adenylate cyclase (AC) activation and concurrent PDE inhibition will increase PC1 levels in ex vivo and in vivo models of PWS, and may consequently increase prohormone processing in the Snord116$^{p-/m+}$ mouse model of PWS. Because mice with a paternal deletion of Snord116 (a mouse model of PWS) have impaired processing of proinsulin to insulin associated with reductions in PC1 transcript and protein, islets will be isolated from wild type (WT) and Snord116$^{p-/m+}$ mice and the responses of these cells to Forskolin, Theophylline, and Forskolin+Theophylline will be analyzed. The same manipulations and measurements will be performed as for iPSC-derived β-cells. If proinsulin processing can be rescued in isolated islets from Snord116$^{p-/m+}$ mice as compared to WT littermates, then investigations of proinsulin processing rescue in Snord116$^{p-/m+}$ mice treated with Forskolin, Theophylline, and Forskolin+Theophylline, in vivo will be conducted.

The present results illustrate that Snord116$^{p-/m+}$ mice have reductions in proinsulin processing to insulin that are associated with reduced PC1 and PC2 content in the islets (FIGS. 3E-G). Furthermore, proghrelin processing is also impaired in the stomachs of Snord116$^{p-/m+}$ mice as well as the processing of proGHRH to GHRH in the hypothalami of Snord116$^{p-/m+}$ mice compared to WT littermates (FIGS. 3I-J). Furthermore, the ratio of proinsulin to insulin is elevated in fasted individuals with PWS compared to age and BMI matched controls, suggesting an impairment in the processing of proinsulin to insulin (FIG. 3H).

Isolated islets from Pa null and heterozygous mice will be included as a control for impaired proinsulin processing as well as a predicted negative response to pharmacological treatment. Peripheral levels of glucose, proinsulin, insulin, and c-peptide will be measured at fasting, and 15, 30, 60, and 120 minutes following intraperitoneal glucose injection. Optimal duration of pharmacological treatment in Snord116$^{p-/m+}$ and WT mice prior to peripheral measures of proinsulin processing will be established empirically. Pa null and heterozygous mice will be included as a control for impaired proinsulin processing in in vivo experiments as well. The initial time periods for testing will be 3 days, 1 week, and 1 month. Several methods of drug delivery will also be tested.

Assays that can distinguish between proghrelin and mature ghrelin, and can thus be used to measure proghrelin processing in the circulation will be developed for both human and mouse. Proghrelin processing following the in vivo pharmacological treatments described above in Snord116$^{p-/m+}$, PC1 null, PC1 heterozygous, and WT animals will be measured.

The hypothalami of Snord116$^{p-/m+}$, WT, and Pa null and Pa heterozygous mice treated with Forskolin, Theophylline, and Forskolin+Theophylline, and measure protein levels of PC1, POMC, αMSH, β-endorphin, and ACTH will be analyzed in order to assess whether in vivo treatment can affect levels of PC1 and POMC processing.

Because Snord116$^{p-/m+}$ animals are runted and do not develop obesity, the main model by which POMC processing will be assessed is the iPSC-derived human neurons, in which more extreme downregulations of NHLH2 and PC1 are observed. However, PC1 and POMC responses to these pharmacologic agents may also be analyzed in primary neurons from young WT POMC-GFP mice. POMC-expressing neurons can be specifically isolated using mice in which POMC neurons express GFP. We will knock down Pcsk1 as a control for impaired POMC processing. We may also try to knock down specific isoforms of Snord116 in vitro using siRNA- or 2-O-methyl-modified anti-sense oligo-based approaches; siRNA are small, double-stranded interfering RNAs that are commonly used to knock down cytoplasmic RNAs, while 2-O-methyl-modified anti-sense oligos are used to knock down snoRNAs which typically are found in the nucleolus (Liang et al. 2011). We will then measure PC1 levels and POMC processing levels and investigate whether pharmacological treatment can increase levels of PC1 and increase POMC processing in the primary mouse neurons in which Snord116 has been knocked down relative to WT.

Additionally, mice with conditional hypomorphic alleles of SNORD116 will be obtained or created. Adult animals with such alleles will have Snord116 acutely reduced in specific hypothalamic nuclei (e.g. the arcuate nucleus) by introduction of suitable cre-expressing constructs, including those driven by specific promoters, eg. For POMC. This approach will circumvent the somatic developmental effects (stunting) of Snord116 hypomorphism in mice.

Effect of cyclase activator and/or phosphodiesterase inhibitor=50% or greater increase in relevant prohormone processing in at least one model tested: PWS iPSC-derived neurons, PWS iPSC-derived β-cells, Snord116$^{p-/m+}$ isolated islets, Snord116$^{p-/m+}$ circulating prohormones, or Snord116-knockdown primary neurons. These phenotypes would be accompanied by increases in relevant transcripts and/or proteins in the affected cells.

Cyclase Activation

Figure 5A:
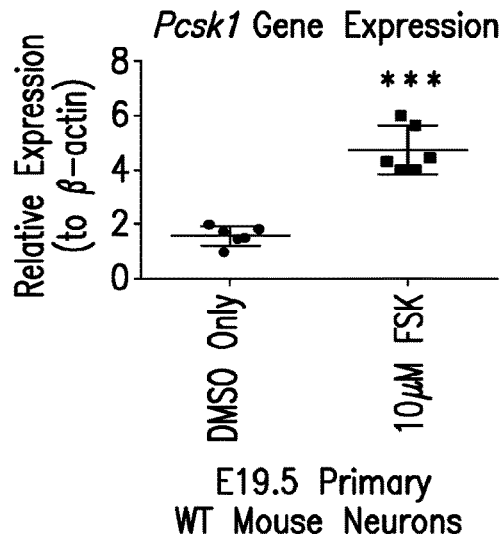
FIGS. 5A-H are graphs showing that the application of Forskolin, an AC agonist, elevates PCSK1/Pcsk1 transcript levels in primary mouse neurons, iPSC-derived neurons, and primary mouse pancreatic islets.

Forskolin was applied to various cellular models and the results illustrate that it robustly and reliably increases PCSK1 transcript levels, PC1 protein levels, and functionally increases prohormone processing. PCSK1/Pcsk1 transcript levels increased between 2-3 fold in iPSC-derived neurons and primary mouse neurons exposed to 10 μM Forskolin (FIGS. 5A, C, D).

Figure 5B:
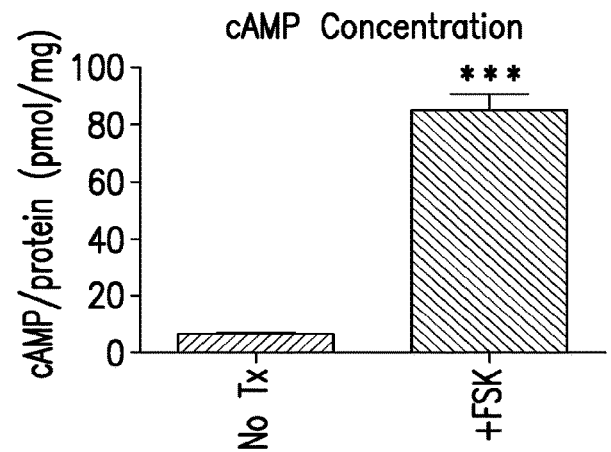
Figure 5C:
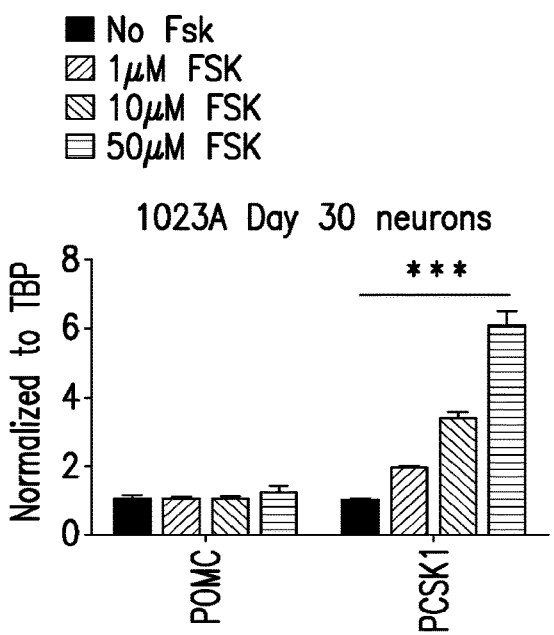
Figure 5D:
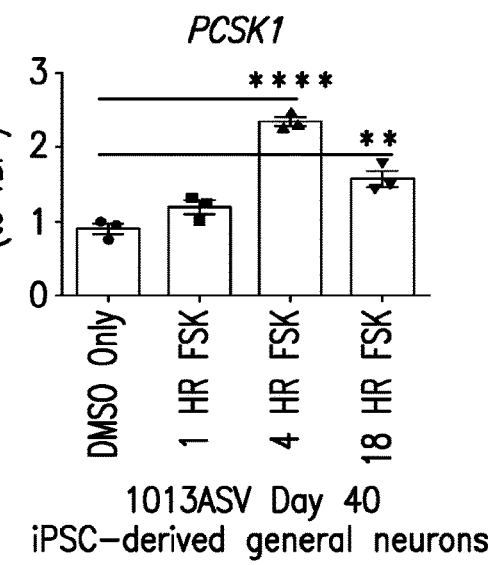
Figure 5E:
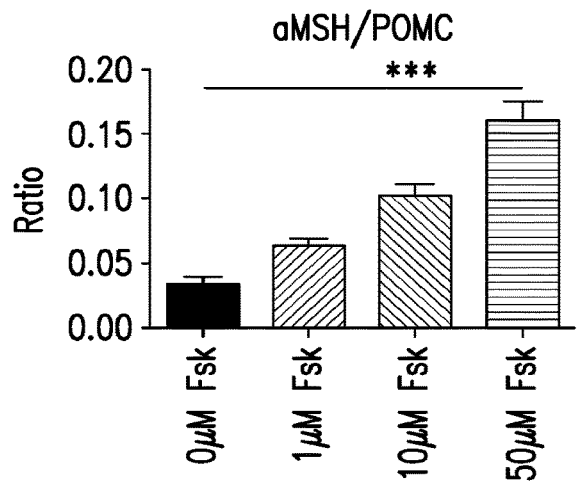
Figure 5F:
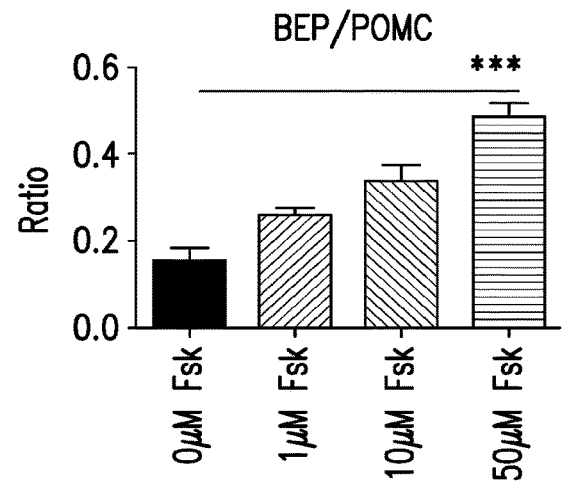
Figure 5G:
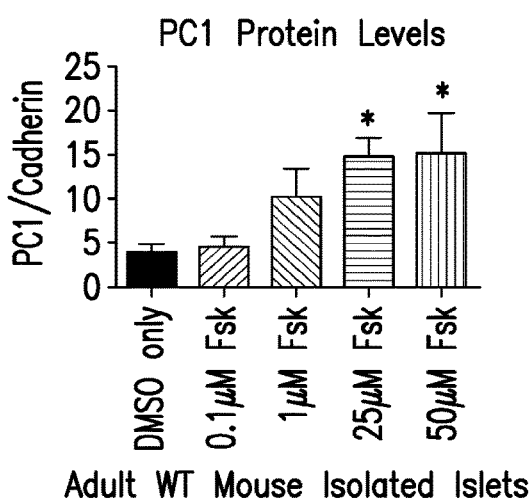
Figure 5H:
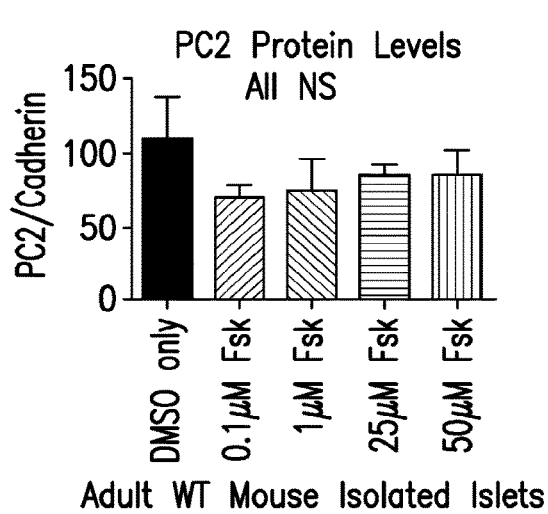

Cyclic AMP concentrations increased about 8.5-fold in iPSC-derived hypothalamic ARC neurons exposed to 10 μM Forskolin, supporting the inference that application of Forskolin increases PCSK1 transcript levels by raising cellular cAMP levels which in turn activate PCSK1's cAMP-response element promoter. FIG. 5A is a graph showing primary forebrain neurons were isolated from gestational day 19.5 (E19.5) embryos of wild type mice and cultured for 72 hours. Subsequently, cells were exposed to either 10 μM Forskolin or its vehicle, dimethyl sulfoxide (DMSO) for 20 hours. Pcsk1 transcript increased ~2.5-fold in primary neurons exposed to Forskolin. FIG. 5B is a graph showing unaffected control hypothalamic arcuate-like (ARC) neurons (Hes Nkx2-1 hESC line) at day 37 (D37) of differentiation were treated with 10 μM Forskolin or vehicle for thirty minutes. Cyclic adenosine monophosphate (cAMP) levels were increased about 8.5-fold in cells exposed to Forskolin. FIG. 5C is a graph showing exposure of unaffected control hypothalamic iPSC-derived neurons (line 1023A) at day 30 of differentiation to graded concentrations of Forskolin elicits a dose-dependent response in PCSK1 transcript levels. FIG. 5D is a graph showing exposure of iPSC-derived neurons (line 1043D3) to 10 μM Forskolin for multiple time intervals finds that PCSK1 is not significantly upregulated after only 1 hour of exposure, but is significantly upregulated by 4 and 18 hours of exposure. Four hours of exposure yielded the maximal increase in upregulation, about 2.5-fold, of the time points tested. FIGS. 5E-F are graphs showing treatment of unaffected control (1023A) iPSC-derived hypothalamic ARC neurons at day 30 of differentiation with graded concentration of Forskolin identifies a dose-dependent increase in POMC processing to both β-endorphin (βEP) and α-melanocyte stimulating hormone (αMSH). FIGS. 5G-H are graphs showing treatment of isolated islets from adult (8-12 week old) WT mice with multiple concentrations of Forskolin shows upregulation of PC1, but not PC2, protein levels at 25 and 50 μM Forskolin concentrations, respectively.

Treatment with forskolin not only elevated transcript levels but also had functional consequences in that POMC processing to both β-endorphin and αMSH were increased (FIGS. 5E-F). Furthermore, application of Forskolin to isolated islets from wild type mice resulted in ~3-fold increase in PC1 protein levels (FIG. 5G). PC2 protein levels were unaffected (FIG. 5H). Taken together, these results show that PC1 levels increase in response to Forskolin in three separate model systems: iPSC-derived neurons, primary neurons, and isolated islets. Furthermore, Forskolin-induced elevation of PC1 is functionally consequential, resulting in increased levels of prohormone processing.

Phosphodiesterase Inhibition

Figure 6A:
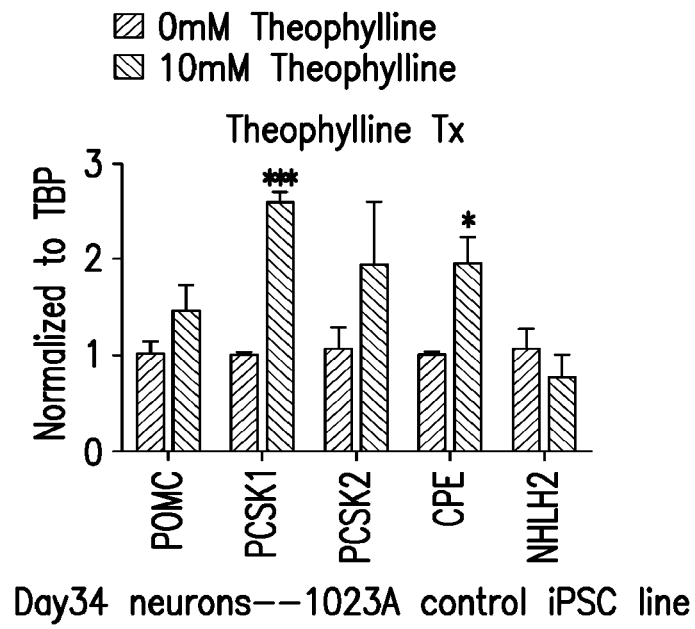
FIGS. 6A-F are graphs showing that application of phosphodiesterase inhibitors to iPSC-derived neurons increases PCSK1 transcript levels and prohormone processing.
Figure 6B:
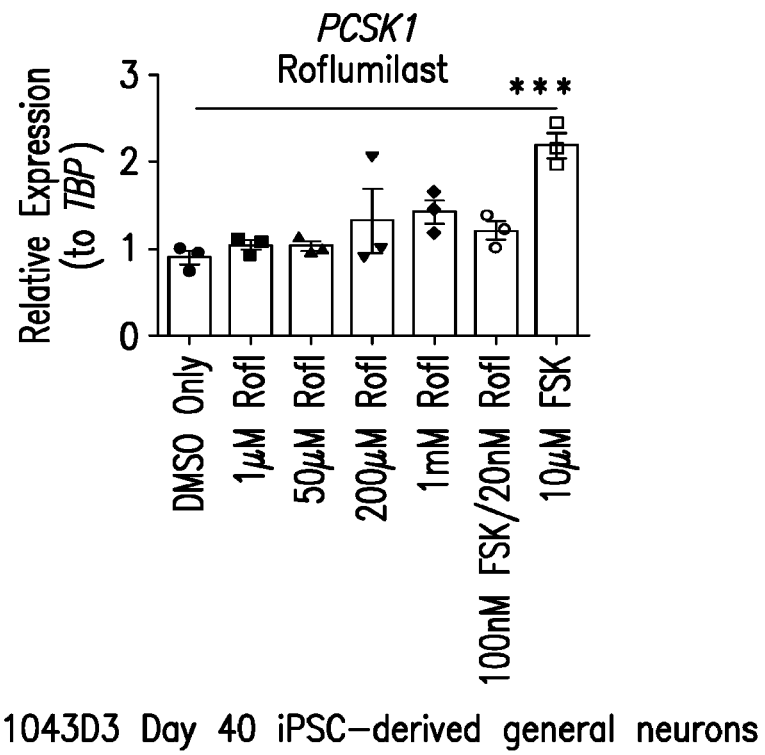
Figure 6C:
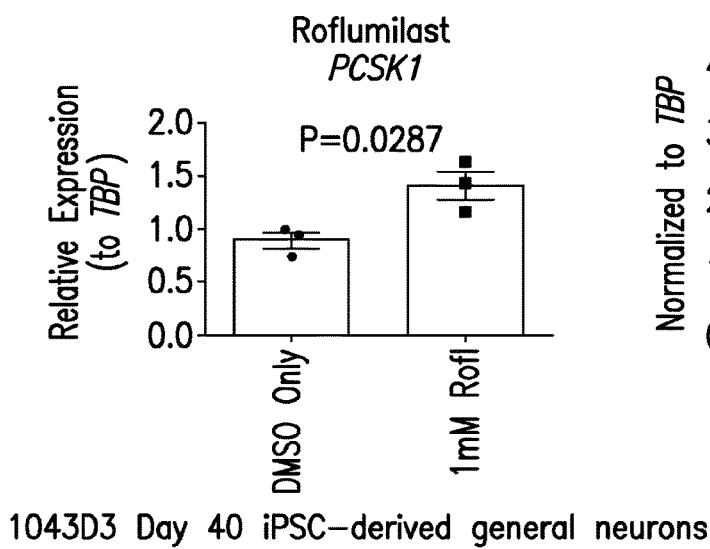
Figure 6D:
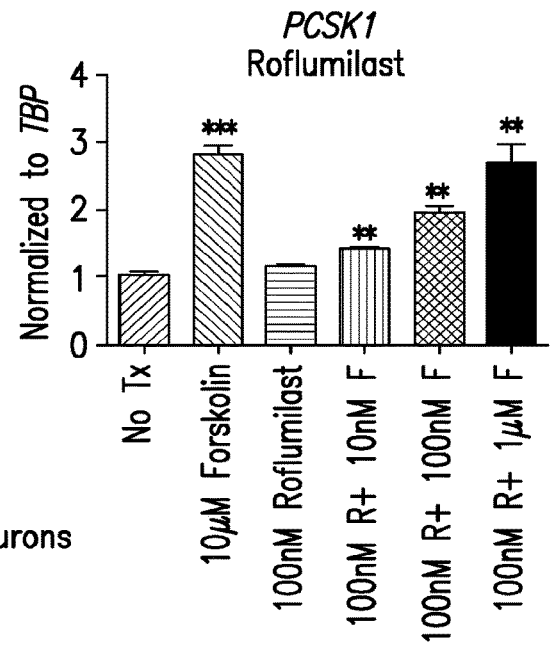
Figure 6E:
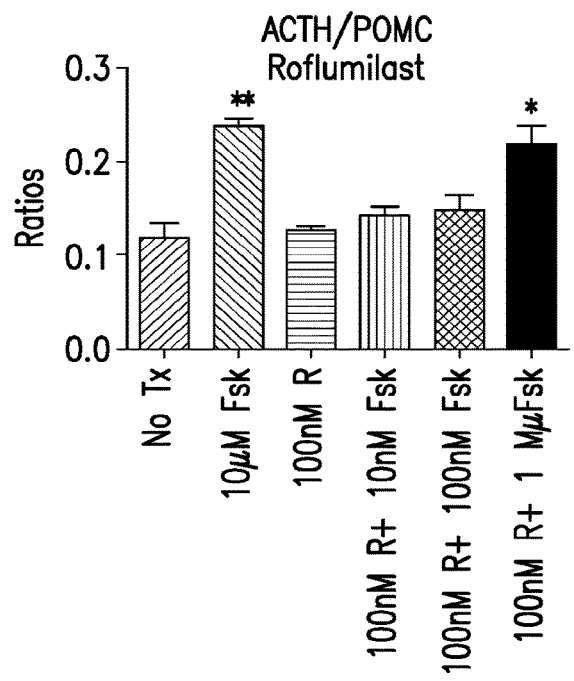
Figure 6F:
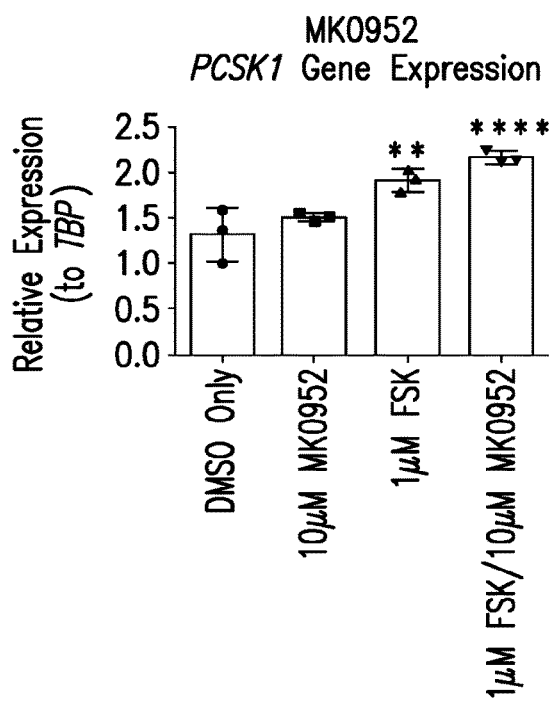

PDE inhibitors have also been tested in iPSC-derived neurons and found that inhibition of phosphodiesterase can also increase transcription of PCSK1. However, the effect size of PDE inhibition on PCSK1 transcript levels is less than that induced by AC agonism with forskolin. Theophylline (10 mM) and Roflumilast (1 mM) both increase PCSK1 transcription as single agents, while MK0952 has thus far only been found to increase PCSK1 transcription in combination with Forskolin in vitro (FIGS. 6A-C, F). Combination treatment with Forskolin and Roflumilast demonstrates that these agents can work together in an additive, possibly synergistic, manner inducing and increased PCSK1 transcription at lower concentrations (1 μM Forskolin, 100 nM Roflumilast) than when either agent is given alone (FIG. 6D). Again, increased PCSK1 transcription due to combination treatment with Forskolin and Roflumilast also increases prohormone processing of POMC to ACTH (FIG. 6E). Specifically, tests with graded concentrations of Forskolin in isolated mouse islets showed a 3-fold upregulation of PC1 protein at 25 μM and 50 μM concentrations. No change in PC2 protein levels were observed in response to Forskolin application. We also found that 10 μM Forskolin applied to primary mouse neurons isolated from E19.5 mice increased Pcsk1 transcript levels ~2-fold.

MK0952

The phenotype most limiting to PWS patients is hyperphagia which is most likely mediated by processes occurring in the central nervous system, particularly the hypothalamus. Thus agents that aim to ameliorate hyperphagia must be able to penetrate the blood brain barrier. MK0952 is an intrinsically potent ($IC_{50}$=0.6 nM) brain-penetrant PDE4 inhibitor with limited whole blood activity ($IC_{50}$=555 nM) (M. Gallant et al. 2010). As described herein, MK0952 is the lead PDE inhibition candidate at present.

Figure 7A:
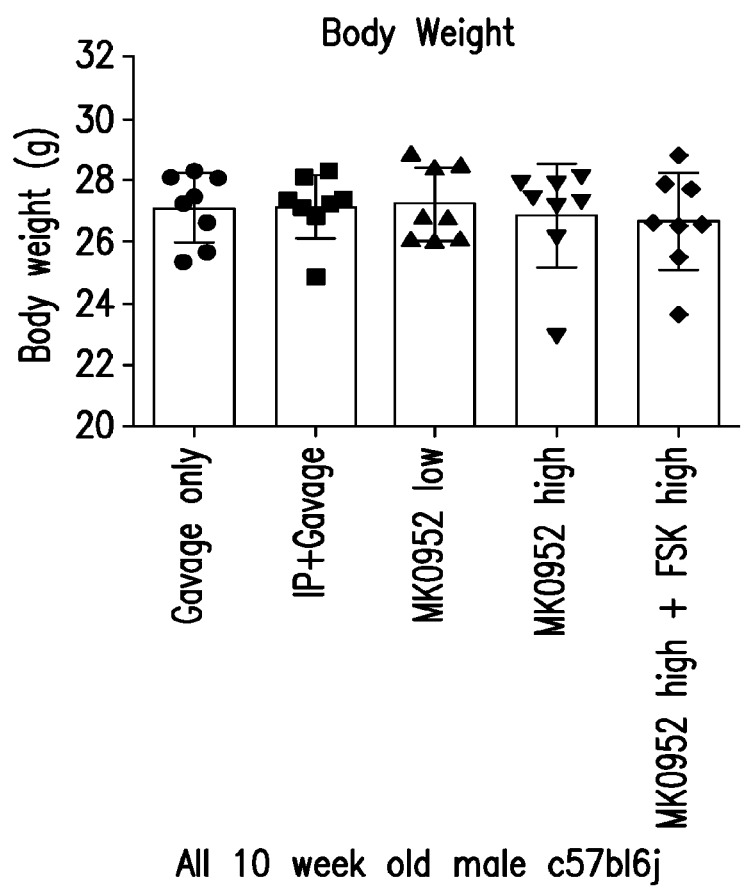
FIGS. 7A-B are graphs showing that a single treatment with MK0952 increases hypothalamic Pcsk1 in wild type mice.
Figure 7B:
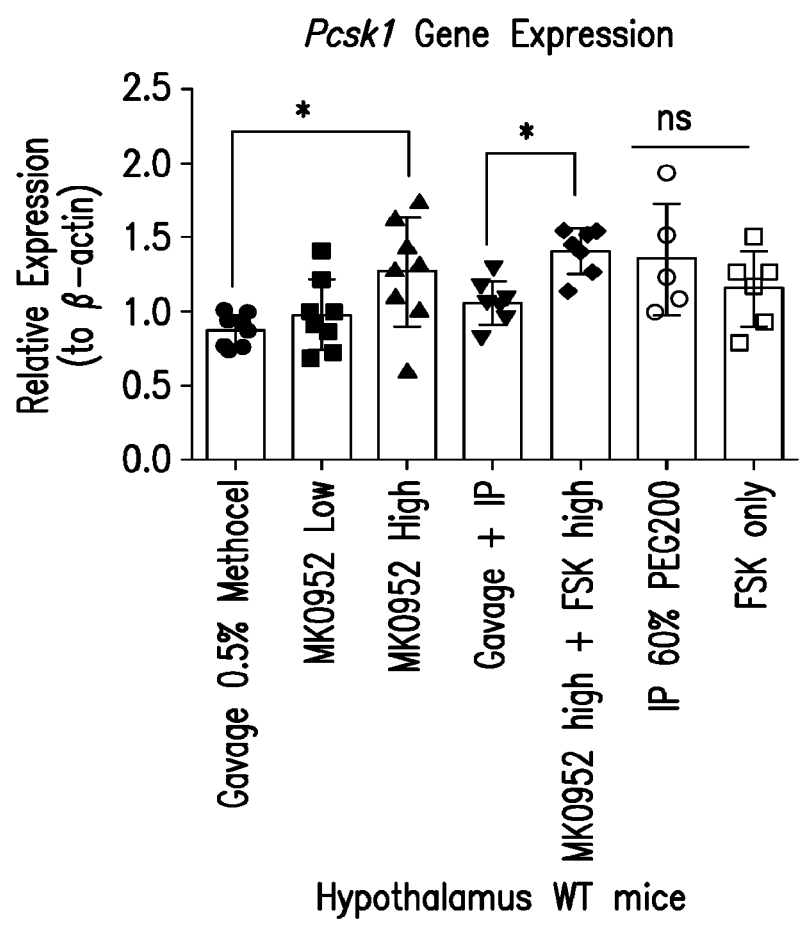

A preliminary in vivo test of MK0952 was performed in wild type mice. A single administration of MK0952 at 10 mg/kg body weight results in a 25% increase in hypothalamic Pcsk1 transcript levels (FIG. 7A). Administration of Forskolin at 25 mg/kg did not result in increased hypothalamic Pcsk1 transcript levels. Co-administration of MK0952 at 10 mg/kg and Forskolin at 25 mg/kg again induced an ~25% increase in hypothalamic Pcsk1 levels, suggesting that this increase was due primarily to the actions of MK0952 (FIG. 7B). We will also analyze circulating cAMP levels, cortical proBDNF/BDNF, cerebellar Pcsk1, gastric Pcsk1, and gastric proghrelin/ghrelin, circulating proinsulin and insulin concentrations (and their ratios), and finally pulmonary Pcsk1 transcript and cAMP levels from these animals as well.

The first in vivo study with MK0952 administered by oral gavage while forskolin was administered intraperitoneally one time to ~4 hour fasted wild type mice was completed. Hypothalamic transcript levels of Pcsk1 were upregulated ~25% following administration of either 10 mg/kg MK0952 as a single agent or both 10 mg/kg MK0952 and 25 mg/kg Forskolin. However, administration of 25 mg/kg Forskolin only did not result in an upregulation of hypothalamic Pcsk1, suggesting the Forskolin at this dose does cannot access the hypothalamus in sufficient quantities to affect Pcsk1 transcription. This also suggests that the increase in hypothalamic Pcsk1 following administration of both 25 mg/kg Forskolin and 10 mg/kg MK0952 was mainly due to the actions of MK0952 in the hypothalamus. This difference likely reflects greater CNS penetrance of the MK0952, not the general relevance of a cyclase activator to therapy of PWS. No change in the ratio of circulating proinsulin:insulin was detected following administration MK0952 or Forskolin. Because the processing of proinsulin to insulin is already quite efficient in WT animals, it is in hindsight unlikely that it would further increase at fasting. However, these 'baseline' data are still valuable for assessing proinsulin to insulin processing under the setting of an intraperitoneal glucose tolerance test at 3 mg/kg glucose in both WT and Snord116$^{p-/m+}$ mice. Additionally, samples were collected for measurement of circulating cAMP levels, cortical proBDNF/BDNF, cerebellar Pcsk1, gastric Pcsk1, and gastric proghrelin/ghrelin, and finally pulmonary Pcsk1 transcript and cAMP levels.

Example 3

Clinical Study of Compounds in Patients with Prader Willi Syndrome (PWS)

The preliminary design of the proposed clinical study for individuals with PWS is based on the hypothesis that the expression of proconvertase 1 (PC1) in decreased in the neurons of individuals with PWS (Burnett et al. 2017). Experimental in vitro and in vivo exposure to adenylate cyclase agonists and PDE4 inhibitors causes up-regulation of PC1 expression and activity in human stem cell-derived and rodent forebrain neurons, and human fibroblasts. It is anticipated that administration of these drugs will increase the conversion of implicated prohormones to active hormones.

The clinical study will address and illustrate the efficacy of the drug in enhancing the activity of PC1 as follows:
1. To illustrate the effects of the candidate therapeutic agents on the behavioral and the endocrine phenotypes of PWS.
2. To monitor the clinical safety profile of such agents.

Figure 8A:
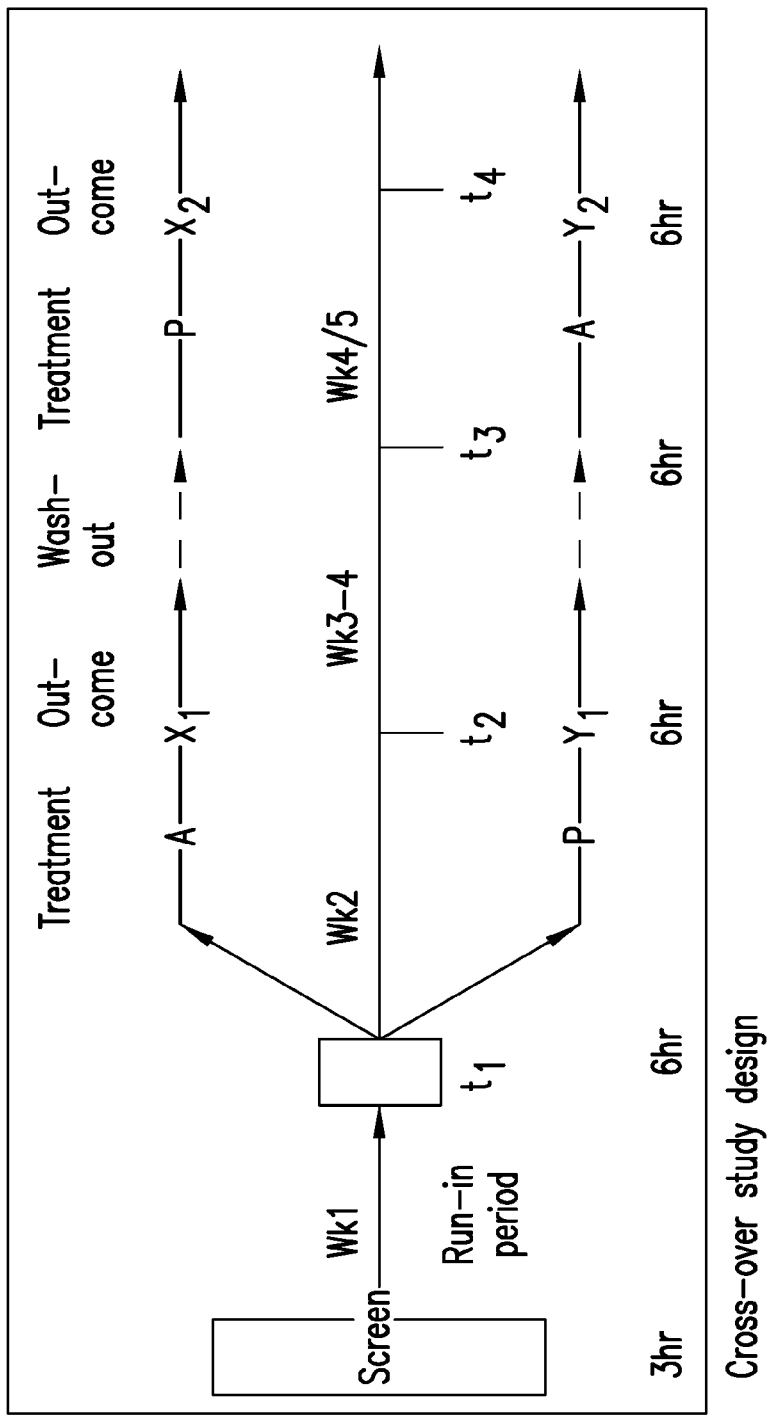

Study Design:

The clinical study will utilize a cross-over study design (Cleophas et al. 2006, Wellek and Blettner 2012, and Louis et al. 1984). This design provides the power to assess the effect of treatment accounting for the variability between subjects in a small cohort (FIG. 8A). The washout period between the two treatment arms will mitigate carryover effects; the short duration of the study minimizes the "time-effects" (effects on the change in disease process over time).

Inclusion Criteria*:
1. Genetically proven diagnosis of PWS
2. Age>18 years
   *Recombinant growth hormone therapy is permissible.

Exclusion Criteria:
1. Severe psychiatric disorder
2. Uncooperative to take the medication
3. Systemic illness, e.g. serious gastrointestinal illness like inflammatory bowel disease, cardiac disease, especially rhythm disturbances, diagnosis of diabetes, hepatic or renal disease or failure.
4. Anemia defined as hemoglobin<10 gm/dL
5. Patients on drugs that have potential interaction with the target drug, e.g. PDE4 inhibitors interact with anti-seizure medications, cimetidine, omeprazole, antibiotics etc. Many of these drugs alter hepatic enzyme activity and could interfere with the metabolism of a PDE4 inhibitor. A complete list of exclusion drugs will be based on the pharmacokinetic and pharmacodynamic properties of the identified therapeutic agent.

Recruitment: The recruitment of the subjects will be facilitated by partnership with the PWS Foundation (FPWR and PWSA), patient support groups and the clinicians caring for children with PWS. Phone screening will identify potentially eligible subjects who will be invited for the screening visit.

The study will last for 4-6 weeks and consist of the following visits:
1. Screening visit: At this visit, a complete review of medical records, medications and physical examination will be performed along with screening lab measurements (from FIG. 8B, same as safety profile aside from the drug level). Subjects will be provided a week of placebo for the run-in period to assess compliance. This will be a short outpatient visit (~3 hours). All other study visits will be 6-8 hours long short in-patient stay.
2. Baseline visit (t1 and t3 from FIG. 8A): Subjects who successfully complete the run-in period will be invited to participate in the study. The eligible subjects will be randomized to either the AP group, or the PA group (FIG. 8A). Subjects will be advised to fast for >8 hours for the visit. Physical profiling will include height, weight, body fat measurement, vital signs, resting energy expenditure and a complete physical examination. A complete pituitary profile that includes ACTH, cortisol, FSH/LH, estrogen/testosterone, TSH/free T4, GH, IGF-1, IGFBP3 will be performed. The subjects will undergo a mixed meal tolerance test (MMTT) with standardized meal and blood measurements will be obtained at 0,30,60,90,120 and 180 minutes from an indwelling IV catheter (FIG. 8B).

The primary guardians will complete questionnaires relating to hyperphagia (Dykens or modified Dykens) and behavioral assessment will be performed using the Oxytocin Study Questionnaire (25-28). In addition to this, they will complete a food frequency questionnaire on 3 separate days to include at least one weekend. The visit is expected to last 6-8 hours. Study medication for 1 week will be dispensed with caregiver instruction.
3. Follow-up visit (t2 and t4 from FIG. 1): The subject will return for a follow-up visit in 1 week after the initiation of the study medication. The measurements mentioned above will be repeated at this visit, and a medication count will be obtained, along with structured questionnaire for the assessment of toxicity. Each of these visits will be 6-8 hours. A washout period of 1-2 weeks will be allowed prior to the $2^{nd}$ phase of the study.

Outcome Measures:
1. Hormonal profile in response to a standard meal: Based on the effect of PC1 on conversion of prohormones (such as proinsulin to insulin etc.), it is anticipated that administration of the drug will cause an increase in the ratio of prohormone:hormone (e.g. proinsulin: insulin) (Burnett et al. 2017). This will be tested by hormonal response to a standard MMTT. MMTT is performed by administration of a liquid meal (6 cc/kg of Boost or equivalent to a maximum of 360 cc) followed by periodic measurement of insulin, proinsulin, POMC prohormone, ACTH, AgRP, proglucagon, glucagon, GLP1, oxytocin (and propeptide), ghrelin, proghrelin, free fatty acids, and glucose. MMTT has been validated in clinical studies of subjects with PWS (P. Gumus Balikcioglu et al. 2015).

Relative to values obtained prior to drug administration, it is anticipated that there will be an absolute increase in insulin release, decrease in proinsulin release and an increase in insulin/proinsulin ratio. All in 25% range. It is also expected that glucose concentrations will be decreased by 15-20 and ffa as well. In plasma obtained prior to the MMT, it is anticipated that POMC will be increased and AgRP reduced by ~25%. Oxytocin should be increased by 15-20% as well. It is also anticipated that proghrelin/ghrelin ratio will be reduced. Spinal fluid may also be examined/studied in these subjects as well, but would not be evaluated in relationship to a meal. The following components may be assayed: pomc prohormone, beta endorphin, alpha msh, AgRP and oxytocin, anticipating that the drugs would reduce pomc prohormone, and increase beta endorphin, alpha msh and oxytocin, and reduce AgRP in comparison to untreated subjects.
2. Pharmacometabolomic profile: Metabolomic profiling provides an additional opportunity to understand the effects of the drug on the metabolic phenotype. Metabolomic profile of the study subjects before and after treatment with the drug will be performed to identify biomarkers for a) response to treatment in the pathways of interest, viz. insulin metabolism pathway and others, b) to identify individual differences in treatment, by identification of pathways selectively up- or down-regulated in different individuals, and c) identify the profiles of side-effects or toxicity using a pathway based analysis that may not be obvious by the standard study of established larger molecular profiling (R. Kaddurah-Daouk, R. Weinshilboum, N. 2015; R. D. Beger et al. 2016).
3. Changes in Hyperphagia related behavior: The Dykens (and modified Dykens) questionnaire assesses the behavior, severity and drive for hunger. In addition to these outcomes, the Oxytocin Behavior Questionnaire will assess social and emotional behavior related with eating. These outcomes will be supplemented with the analysis of the food frequency questionnaires. It is expected that treatment will also improve behavior and/or emotional state.

Sample size: A pilot sample size of 6 subjects will be recruited for this study. The power of this sample size to detect outcomes of interest will depend on the effect size ascertained by in vivo hormonal or pharmacometabolomic profiling in animal models. As reflected in FIG. 8C, an effect size of ~1.47 is required to detect a significant change in a cohort of 6 subjects. The effect size is calculated as the difference in the means of the observation with the placebo as compared to the active drug divided by the standard deviation of the change. As each subject serves as his/her own control, the crossover study design limits the variability and allows reaching power in ¼ of the subjects for a similar parallel arm study design.

Additional Study Information:
1. Based on the prior studies in children with PWS and the need to achieve high effect size, the standard mixed meal has been selected for the study.
2. The study will be conducted in the outpatient facility of the Irving Institute for Clinical and Translational Research.
3. An IRB protocol for the study will be prepared directed to the appropriate PDE inhibitor and/or cyclase activator.
4. The metabolomic profiling—if obtained in this preliminary study—will be performed in the Hormone and Metabolite Core of the Diabetes and Endocrinology Research Center.

Example 4

Methods of Treating Prader-Willi Syndrome—Combination Therapy of Endogenous and Exogenous MC4R Agonism.

Individuals with PWS will be treated using agents that increase endogenous levels of processed hormones by virtue of increasing PC1 production through raising levels of cellular cAMP production and/or blocking its degradation.

In the arcuate nucleus, POMC is processed to αMSH by proconvertase 1 (PC1) (S. L. Wardlaw 2011). αMSH is an endogenous ligand of the melanocortin 4 receptor (MC4R). Humans and mice with inactivating mutations in POMC, PCSK1 (gene product of PCSK1 is PC1), or MC4R are hyperphagic and obese (C. Vaisse et al. 1998). Mutations in MC4R are the most common single gene cause of obesity in humans (R. J. Loos et al. 2008). AgRP is also produced in the arcuate nucleus and is an inverse agonist at MC4R. ProAgRP is processed to AgRP by PC1 (S. L. Wardlaw 2011).

Figure 4:
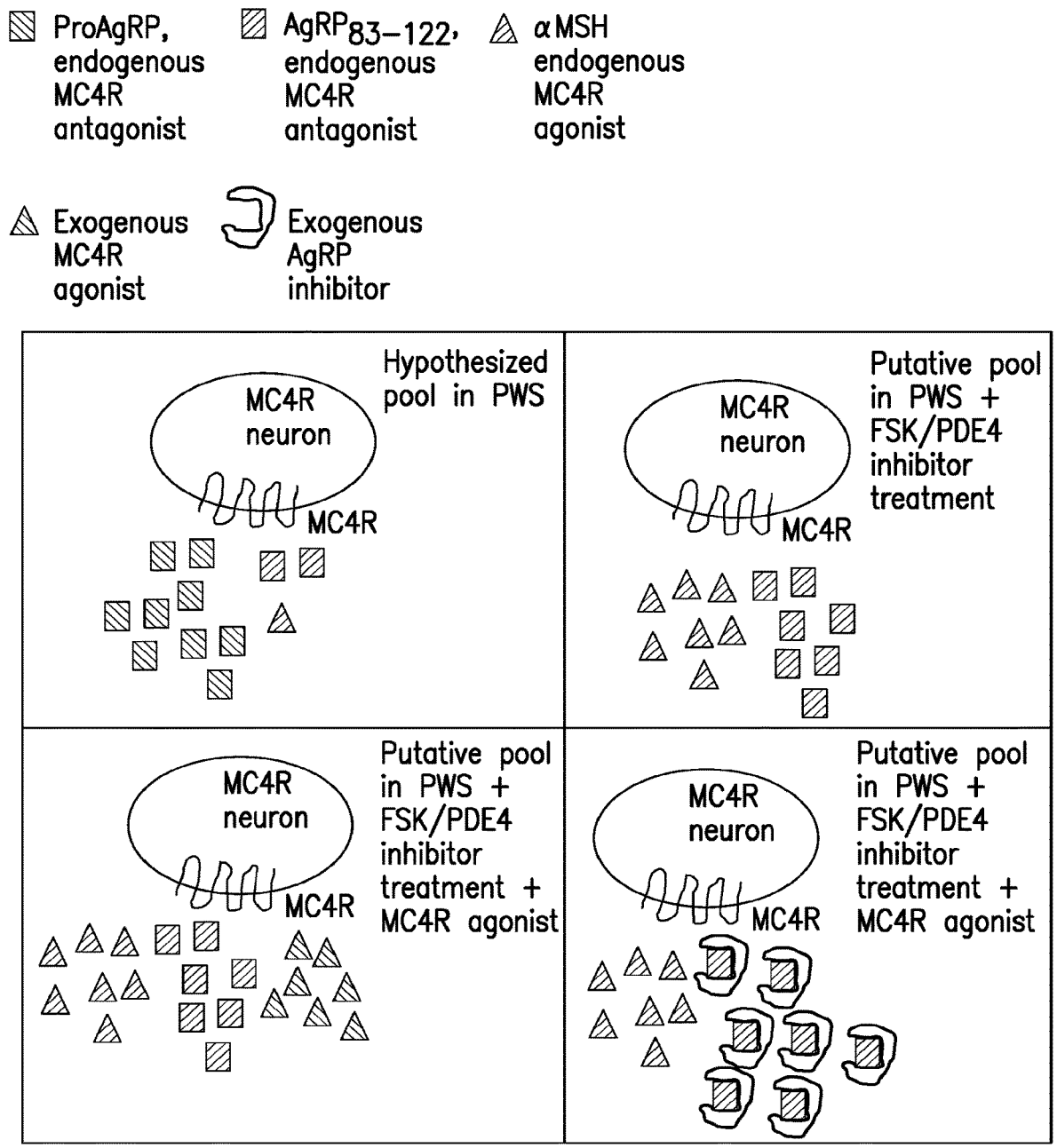
FIG. 4 is a schematic showing the therapeutic rationale for co-administration of MC4R agonists and/or AgRP inhibitors in combination with Forskolin and/or Theophylline in individuals with PWS and possibly other types of obesity, including common obesity.

It is possible that increases in PC1 production may increase the production of both αMSH and AgRP, which have opposite effects at MC4R (FIG. 4). The use of small molecule or peptide-based MC4R agonists could help to ensure that the extracellular pools of agents that agonize MC4R are in excess of those that antagonize MC4R (FIG. 4, Table 3). This would be expected to push signaling at the MC4R towards anorexigenic responses (FIG. 4). Agents that bind to AgRP and block its effects at MC4R could also be a useful strategy in this setting (Table 3) (E. C. Lee and P. A. Carpino 2016). Compounds that act similarly that are not mentioned in Table 3 may also be useful. This strategy may be efficacious not just for treating PWS, but also other forms of monogenic/syndromic obesity as well as common obesity.

human stem cell-derived neurons, mouse primary neurons, and increases PC1 protein level in mouse isolated islets. Furthermore, Forskolin treatment also increases POMC prohormone processing in stem cell-derived hypothalamic neurons. Application of PDE inhibitors Theophylline and Roflumilast to stem cell neurons increases PCSK1 transcript levels both as single agents and in combination with Forskolin. Combination treatment of Roflumilast and Forskolin also additively increases POMC prohormone processing (to anorexigenic peptides) in stem cell hypothalamic neurons. Treatment of stem cell-derived neurons with both Forskolin and MK0952 (a class 4 PDE inhibitor) increases PCSK1 mRNA. Finally, a single oral dose of 10 mg/kg MK0952 increases hypothalamic Pcsk1 transcript levels by 25% in wild type mice. Longer applications of MK0952 in vivo in both wild type and mice hypomorphic for paternal Snord116 will be tested next. In addition we will collaborate with Andrea Haqq and colleagues to measure circulating pro- and processed hormone levels (e.g. proinsulin, POMC, pro-oxytocin, proBDNF) in individuals with PWS and matched controls.

Also provided is a protocol for preliminary clinical study of MK0952 and other candidate compounds in individuals with PWS. The major aims of this clinical study will be to monitor the clinical safety profile of these agents in PWS subjects as well as to measure behavioral and neuroendocrine endpoints to assess preliminary efficacy.

TABLE 3

Example Compounds that could be co-administered with FSK and PDE Inhibitors

| Drug Name | Company | Mechanism of Action | Notes |
| --- | --- | --- | --- |
| RM-493 (Setmelanotide) | Rhythm Pharmaceuticals and Ipsen pharmaceuticals (Ipsen patented slow-release formula) | Peptide-based analog of α-MSH | Currently in Phase II clinical trials for treatment of hyperphagia in PWS, reported that does not have off-target cardiovascular effects, administration via subcutaneous injection |
| TTP2515 | Transtech Pharma | Small molecule, non-peptide AgRP$_{83-122}$ antagonist, does not block activity of αMSH | Decreases food intake and weight gain in lean mice on high fat diet |
| 2-aminothiazole derivatives | Transtech Pharma | Alternative formulations of above TTP2515 | |
| MK-0493 | Merck | Small molecule, non-peptide MC4R agonist | Robust weight loss in animal models but limited efficacy for weight loss in non-genetic obese; possible that individuals with PWS may have increased sensitivity to such agents, no observed cardiovascular side effects, oral formulation |

Summary/Conclusions

Although the gene encoding PC1, PCSK1, is downregulated in cell based and animal models of PWS, the gene itself is intact and thus could be subject to pharmacological manipulation. The present data provides results of ongoing preclinical studies to pharmacologically manipulate cellular levels of PCSK1/PC1. In vitro experiments demonstrate that application of Forskolin, an adenylyl cyclase agonist robustly and reliably upregulates PCSK1 expression in

REFERENCES

Conkright, M. D. et al. Genome-Wide Analysis of CREB Target Short Article Genes Reveals A Core Promoter Requirement for cAMP Responsiveness. *Molecular Cell* 11, 1101-1108 (2003).

Udupi, V., Townsend, C. M. & Greeley, G. H. Stimulation of Prohormone Convertase-1 mRNA Expression by Second Messenger Signaling Systems. *BIOCHEMICAL AND BIOPHYSICAL RESEARCH COMMUNICATIONS* 246, 463-465 (1998).

Tang, W.-J. & Hurley, J. Catalytic Mechanism and Regulation of Mammalian Adenylyl Cyclases. *Molecular Pharmacology* 54, 231-240 (1998).

Tesmer, J. J. G. et al. Two-Metal-Ion Catalysis in Adenylyl Cyclase. *Science* 285, 756-760 (1999).

Onda, T. et al. Type-specific regulation of adenylyl cyclase. Selective pharmacological stimulation and inhibition of adenylyl cyclase isoforms. *J Biol Chem* 276, 47785-47793, doi:10.1074/jbc.M107233200 (2001).

Liang, X. H., Vickers, T. A., Guo, S. & Crooke, S. T. Efficient and specific knockdown of small non-coding RNAs in mammalian cells and in mice. *Nucleic Acids Res* 39, e13, doi:10.1093/nar/gkq1121 (2011).

Sunahara, R. K. & Taussig, R. Isoforms of Mammalian Adenylyl Cyclase: Multiplicities of Signaling. *Molecular Interventions* 2, 168-184 (2002).

S. L. Wardlaw, Hypothalamic proopiomelanocortin processing and the regulation of energy balance. *European journal of pharmacology* 660, 213-219 (2011).

C. Vaisse, K. Clement, B. Guy-Grand, P. Froguel, A frameshift mutation in human MC4R is associated with a dominant form of obesity. *Nature Genetics* 20, 113-114 (1998).

R. J. Loos et al., Common variants near MC4R are associated with fat mass, weight and risk of obesity. *Nat Genet* 40, 768-775 (2008).

E. C. Lee, P. A. Carpino, Melanocortin-4 receptor modulators for the treatment of obesity: a patent analysis (2008-2014). *Pharmaceutical Patent Analyst* 4, 95-107 (2016).

Fimia G M, Sassone-Corsi P. 2001. Cyclic AMP signaling. *J Cell Sci* 114: 1971-1972.

L. C. Burnett et al., Deficiency in prohormone convertase PC1 impairs prohormone processing in Prader-Willi syndrome. *J Clin Invest* 127, 293-305 (2017).

F. D. P. Deborah J. Good, Kathleen A. Mahon, Albert F. Parlow, Heiner Westphal, Ilan R. Kirsch, Hypogonadism and obesity in mice with a targeted deletion of the Nhlh2 gene. *Nature Genetics* 15, 397-401 (1997).

D. L. Fox, Dissertation, University of Massachusetts Amherst, Ann Arbor, MI (2007).

P. Stijnen, B. Ramos-Molina, S. O'Rahily, J. W. M. Creemers, PCSK1 mutations and human endocrinopathies: from obesity to gastrointestinal disorders. *Endocrine Reviews* 17, (2016).

M. D. Conkright et al., Genome-Wide Analysis of CREB Target Short Article Genes Reveals A Core Promoter Requirement for cAMP Responsiveness. *Molecular Cell* 11, 1101-1108 (2003).

V. Udupi, C. M. Townsend, G. H. Greeley, Stimulation of Prohormone Convertase-1 mRNA Expression by Second Messenger Signaling Systems. *Biochemical and Biophysical Research Communications* 246, 463-465 (1998).

W.-J. Tang, J. Hurley, Catalytic Mechanism and Regulation of Mammalian Adenylyl Cyclases. *Molecular Pharmacology* 54, 231-240 (1998).

J. J. G. Tesmer et al., Two-Metal-Ion Catalysis in Adenylyl Cyclase. *Science* 285, 756-760 (1999).

T. Onda et al., Type-specific regulation of adenylyl cyclase. Selective pharmacological stimulation and inhibition of adenylyl cyclase isoforms. *J Biol Chem* 276, 47785-47793 (2001).

M. Gallant et al., Discovery of MK-0952, a selective PDE4 inhibitor for the treatment of long-term memory loss and mild cognitive impairment. *Bioorganic & Medicinal Chemistry Letters* 20, 6387-6393 (2010).

Q. Zhang, G. J. Bouma, K. McClellan, S. Tobet, Hypothalamic expression of snoRNA Snord116 is consistent with a link to the hyperphagia and obesity symptoms of Prader-Willi syndrome. *Int J Dev Neurosci* 30, 479-485 (2012).

Y. Qi et al., Snord116 is critical in the regulation of food intake and body weight. *Sci Rep* 6, 18614 (2016).

L. Wang et al., Differentiation of hypothalamic-like neurons from human pluripotent stem cells. *J Clin Invest* 125, 796-808 (2015).

V. Grinevich, M. G. Desarmenien, B. Chini, M. Tauber, F. Muscatelli, Ontogenesis of oxytocin pathways in the mammalian brain: late maturation and psychosocial disorders. *Front Neuroanat* 8, 164 (2014).

M. Tauber et al., The Use of Oxytocin to Improve Feeding and Social Skills in Infants With Prader-Willi Syndrome. *Pediatrics* 139, (2017).

R. J. Kuppens, S. H. Donze, A. C. Hokken-Koelega, Promising effects of oxytocin on social and food-related behaviour in young children with Prader-Willi syndrome: a randomized, double-blind, controlled crossover trial. *Clin Endocrinol (Oxf)* 85, 979-987 (2016).

G. Alvarez-Bolado, F. A. Paul, S. Blaess, Sonic hedgehog lineage in the mouse hypothalamus: from progenitor domains to hypothalamic regions. *Neural development* 7, 4 (2012).

S. Blaess, N. Szabo, R. Haddad-Tovolli, X. Zhou, G. Alvarez-Bolado, Sonic hedgehog signaling in the development of the mouse hypothalamus. *Front Neuroanat* 8, 156 (2014).

E. O. Mazzoni et al., Synergistic binding of transcription factors to cell-specific enhancers programs motor neuron identity. *Nat Neurosci* 16, 1219-1227 (2013).

P. Arlotta, O. Hobert, Homeotic Transformations of Neuronal Cell Identities. *Trends Neurosci* 38, 751-762 (2015).

E. S. Deneris, O. Hobert, Maintenance of postmitotic neuronal cell identity. *Nat Neurosci* 17, 899-907 (2014).

T. J. Cleophas, A. H. Zwinderman, T. F. Cleophas, in *Statistics Applied to Clinical Trials*. (Springer Netherlands, Dordrecht, 2006), pp. 219-228.

S. Wellek, M. Blettner, On the Proper Use of the Crossover Design in Clinical Trials: Part 18 of a Series on Evaluation of Scientific Publications. *Deutsches Ärzteblatt International* 109, 276-281 (2012).

T. A. Louis, P. W. Lavori, J. C. I. Bailar, M. Polansky Crossover and Self-Controlled Designs in Clinical Research. *New England Journal of Medicine* 310, 24-31 (1984).

E. M. Dykens, M. A. Maxwell, E. Pantino, R. Kossler, E. Roof, Assessment of Hyperphagia in Prader-Willi Syndrome. *Obesity* 15, 1816-1826 (2007).

S. R. Crawford et al., The International Development of The Modified Hyperphagia Questionnaire. *Value in Health* 18, A761.

J. M. MD, D. D. MD, A. Chen, T. E. Hughes, D. D. Kim, paper presented at the Obesity Week 2014, Boston, MA, 2014.

R. J. Kuppens, S. H. Donze, A. C. S. Hokken-Koelega, Promising effects of oxytocin on social and food-related behaviour in young children with Prader-Willi syndrome: a randomized, double-blind, controlled crossover trial. *Clinical Endocrinology* 85, 979-987 (2016).

P. Gumus Balikcioglu et al., Macronutrient Regulation of Ghrelin and Peptide Y Y in Pediatric Obesity and Prader- Willi Syndrome. *The Journal of Clinical Endocrinology & Metabolism* 100, 3822-3831 (2015).

R. Kaddurah-Daouk, R. Weinshilboum, N. on behalf of the Pharmacometabolomics Research, Metabolomic Signatures for Drug Response Phenotypes: Pharmacometabolomics Enables Precision Medicine. *Clinical Pharmacology & Therapeutics* 98, 71-75 (2015).

R. D. Beger et al., Metabolomics enables precision medicine: "A White Paper, Community Perspective". *Metabolomics* 12, 149 (2016).

The scope of the present invention is not limited by what has been specifically shown and described hereinabove. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill m the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation. The actual scope of the invention is intended to be defined in the following claims.

What is claimed is:

1. A method for treating Prader-Willi Syndrome (PWS) comprising administering a selective phosphodiesterase 4 inhibitor (PDE4i) to a subject with PWS, in an amount that alleviates, eliminates or prevents one or more symptoms of PWS.

2. The method of claim 1, wherein the one or more symptoms comprises hyperphagia, reduced metabolic rate, obesity, hypogonadism, decreased growth hormone production, poor muscle tone, reduced stamina, reduced ability to focus, impaired cognition, anxiety, growth failure, reduced conversion of immature hormones to mature and active forms, or diabetes.

3. The method of claim 1, wherein the one or more symptoms comprises hyperphagia.

4. The method of claim 1, wherein the one or more symptoms comprises reduced conversion to mature and active forms of one or more of insulin, ghrelin, oxytocin, growth hormone releasing hormone (GHRH), brain-derived neurotrophic factor (BDNF) or gonadotropin.

5. The method of claim 1, wherein the selective PDE4 inhibitor comprises theophylline, roflimilast, apremilast, ibdulast, GSK356278, or IBMX.

6. The method of claim 1, wherein the method further comprises administering one or more additional therapeutic agents effective for treating or alleviating one or more symptoms of PWS.

7. The method of claim 1, wherein the method further comprises administering an oxytocin receptor agonist.

8. The method of claim 1, wherein the method further comprises administering insulin, an insulin receptor agonist, ghrelin, a ghrelin receptor agonist, growth hormone-releasing hormone (GHRH), a GHRH receptor agonist, alpha-melanocyte stimulating hormone (alpha-MSH), an alpha-MSH receptor agonist, oxytocin, an oxytocin receptor agonist, orexin, an orexin receptor agonist, Brain-derived neurotrophic factor (BDNF), a BDNF receptor agonist, vasopressin, a vasopressin receptor agonist, Neuropeptide Y (NPY), an NPY receptor agonist, Agouti-related protein (AGRP), an AGRP receptor agonist, gonadotropin, a gonadotropin receptor against, or combinations thereof.

* * * * *